United States Patent [19]
Mechoulam et al.

[11] Patent Number: 5,434,295
[45] Date of Patent: Jul. 18, 1995

[54] NEUROPROTECTIVE PHARMACEUTICAL COMPOSITIONS OF 4-PHENYLPINENE DERIVATIVES AND CERTAIN NOVEL 4-PHENYLPINENE COMPOUNDS

[75] Inventors: Raphael Mechoulam; Aviva Breuer, both of Jerusalem; Anat Biegon, Tel Aviv, all of Israel

[73] Assignees: Yissum Research Development Company, Jerusalem, Israel; Pharmos Corp., New York, N.Y.

[21] Appl. No.: 192,924

[22] Filed: Feb. 7, 1994

[51] Int. Cl.$^6$ .................. A61K 31/22; A61K 31/05; C07C 69/01; C07C 39/17

[52] U.S. Cl. ................................ 560/141; 560/255; 568/734

[58] Field of Search ............... 560/141, 255; 568/734; 514/511

[56] References Cited

U.S. PATENT DOCUMENTS

| | | | |
|---|---|---|---|
| 4,282,248 | 8/1981 | Mechoulam et al. | 514/511 |
| 4,528,144 | 7/1985 | Gutierrez et al. | 562/30 |

OTHER PUBLICATIONS

Mechoulam et al., Prog. Med. Chem., 24: 159–207 (1987).
Devane et al., J. Med. Chem., 35: 2065–2069 (1992).
Feigenbaum et al., Proc. Natl. Acad. Sci. U.S. 86: 9584–9587 (1989).
Shohami et al., J. Neurotrauma, 10: 109–119 (1993).
Bar-Joseph et al., J. Neurochem., 61: 685A (1993).
Choi, Neuron 1: 623–634 (1988).
Rogawski, TIPS 14: 325–331 (1993).
Little et al., J. Pharmacol. Exp. Ther., 247: 1046–1051 (1988).
D'Ambra et al., J. Med. Chem., 35: 124–135 (1992).
Mechoulam et al., J. Med. Chem., 33: 1037–1043 (1990).
McIntosh, J. Neurotrauma, 10: 215–243 (1993).
Eshhar, et al., 5: 237–240 (1993).
Nadler, et al., 622: 79–85 (1993).

*Primary Examiner*—Arthur C. Prescott
*Attorney, Agent, or Firm*—Pennie & Edmonds

[57] ABSTRACT

The present invention provides certain novel 4-phenylpinene derivatives, and teaches how to use said novel derivatives and related compounds in pharmaceutical compositions that have utility in treating various pathological conditions associated with damage to the central nervous system. The active ingredient of the pharmaceutical compositions according to the present invention is a compound of the formula:

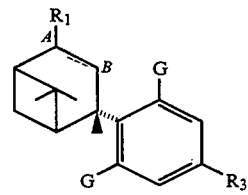

wherein A - - - B designates an optional double bond, $R_1$ designates a variety of organic moieties, G designates alkyl, halogen, or various oxy groups, and $R_3$ designates various alkyl groups, ether groups, or combinations thereof.

33 Claims, 6 Drawing Sheets

☐ VEHICLE  ⧄ HU-270  ⧄ HU-271

NEUROPROTECTIVE PHARMACEUTICAL COMPOSITIONS OF 4-PHENYLPINENE DERIVATIVES AND CERTAIN NOVEL 4-PHENYLPINENE COMPOUNDS

FIELD OF THE INVENTION

The present invention relates to certain novel 4-phenylpinene derivatives. The invention also relates to the incorporation of said novel derivatives and related compounds into pharmaceutical compositions that have utility in treating various pathological conditions associated with damage to the central nervous system. The active ingredient of the pharmaceutical compositions according to the present invention is a compound of the formula:

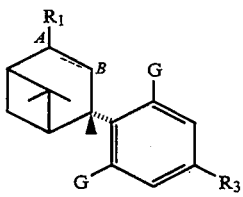

wherein A - - - B designates an optional double bond, $R_1$ designates a variety of organic moieties, G designates alkyl, halogen, or various oxy groups, and $R_3$ designates various alkyl groups, ether groups, or combinations thereof.

BACKGROUND OF THE INVENTION

The structural and stereochemical requirements for activity within the cannabinoid group of compounds is well-established (Mechoulam and Feigenbaum, *Prog. Med. Chem.* 24: 159–207, 1987). Such compounds contain a tricyclic benzopyran ring system with a free phenolic group on C-3' and on alkyl side chain on C-5'. The natural active constituents of cannabis, as well as numerous synthetic analogs with cannabimimetic psychotropic activity are the stereospecific (−) enantiomers, that is the [3R,4R] configuration, of tetrahydrocannabinol (THC).

In contrast, the stereospecific (+) enantiomers, i.e. the [3S,4S] configuration of tetrahydrocannabinols, are generally devoid of cannabimimetic activity. Some of these non-psychotropic THC type compounds with [3S,4S] configuration have been shown to have considerable therapeutic potential, including antiemetic, antiglaucoma, analgesic and neuroprotective effects, as described below.

The major active constituent of cannabis is $\Delta^1$ THC (also named $\Delta^9$ THC by another nomenclature). The 1,1 dimethylheptyl (DMH) homolog of [3R,4R]-7-hydroxy $\Delta^6$ THC, denoted HU-210, is a superpotent agonist with cannabimimetic activity two orders of magnitude higher than the natural $\Delta^1$ THC (Mechoulam and Feigenbaum, Id.).

HU-211 is the (+)-(3S,4S) enantiomer of the synthetic cannabinoid 7-hydroxy-$\Delta^6$-tetrahydrocannabinol 1,1-dimethylheptyl (THC-DMH). In contrast to HU-210 (the (−)-(3R,4R) THC-DMH enantiomer), HU-211 displays a very low affinity to the cannabinoid receptors and is inactive as a cannabimimetic (Devane et al., *J. Med. Chem.* 35: 2065–2069, 1992). Several in vitro and in vivo pharmacological studies have described HU-211 as a functional N-methyl-D-aspartate (NMDA) receptor antagonist and neuroprotective agent.

HU-211 was shown to block NMDA-induced tremor, seizures and lethality in mice. (Feigenbaum et al., *Proc. Natl. Acad. Sci. U.S.* 86: 9584–9587, 1989). Application of HU-211 to rat brain cortical membrane preparations blocked the increase in binding of $^3$H-labeled N-[1-(2-thienyl)-cyclohexyl]piperidine ([$^3$H]TCP) induced by polyamines, glutamate or glycine. Furthermore, HU-211 was shown to block the NMDA induced uptake of $^{45}Ca^{++}$ ions into primary rat forebrain cell cultures suggesting that HU-211 inhibits the influx of calcium ions across the NMDA receptor linked ion channel (Nadler et al., Brain Res. in press, 1993). Administration of HU-211 to rats with closed head injury, a model of head trauma, significantly reduced the extent of edema formation and overall neurological damage (Shohami et al., *J. Neurotrauma* 10: 109–119, 1993). Moreover, HU-211 was shown to prevent neuronal cell damage produced in the CA1 hippocampal region in gerbils caused by common carotid artery occlusion (CCAo) when injected after the ischemic insult (Bar-Joseph et al., *J. Neurochem.* 61: S65A, 1993).

It has been well documented that excessive stimulation of excitatory amino acid receptors, mainly those of the NMDA receptor subtype, is closely involved in processes of central neuronal toxicity and degeneration (Choi, *Neuron* 1: 623–634, 1988). The therapeutic potential of excitatory amino acid antagonists has been proposed for a wide variety of acute or chronic neurological disorders (Rogawski, *TIPS* 14: 325–331, 1993). As an NMDA receptor antagonist, HU-211 can prevent or ameliorate excitotoxic neuronal damage associated with ischemia, anoxia and head trauma.

In the last few years, several groups of compounds which structurally cannot be looked upon as classical cannabinoids have been found to produce cannabimimetic effects, for example the compounds CP-55940 [Little et al., *J.Pharmacol.Exp.Ther.*, 247, 1046–1051 (1988)], pravadoline [D'Ambra et al., *J.Med. Chem.*, 35, 124–135 (1992)], and HU-250 [Mechoulam et al., *J.Med. Chem.* 33, 1037–1043 (1990)]. See also Mechoulam et al. U.S. Pat. No. 4,282,248.

A new family of compounds has been discovered that exhibits a pharmacological profile of activities related to that of HU-211. Unlike classical cannabinoids, these compounds lack the typical 6-membered oxygen-containing benzopyran ring. The new family of compounds may be exemplified by (+)-4-[4-DMH-2,6 diacetoxyphenyl]-2-carboxy-6,6-dimethylbicyclo[3.1.1]hept-2-en, herein denoted HU-259. The stereochemistry at C-1 is S. The protons at C-1 and C-5 are cis and at C-5 and C-4 are trans. Thus, the stereochemistry parallels that of HU-211.

SUMMARY OF THE INVENTION

The present invention provides methods for treatment various pathological conditions including (but not limited to) acute injuries to the central nervous system ("CNS") associated with excitatory amino acid neurotoxicity, chronic degenerative disease associated with selective neuronal loss, and CNS poisoning. These methods involve the use of appropriately formulated pharmaceutical compositions with neuroprotectant activity which contain as their active ingredient a compound of the formula:

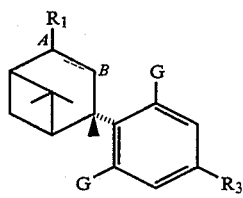

In the above formula, the dotted line A - - - B indicates an optional bond. The variable substituents $R_1$, G, and $R_3$ are defined as follows: $R_1$ is (a) —R'N(R'')$_2$ wherein R' is $C_1$–$C_5$ alkyl and each R'', which may be the same or different, is hydrogen or $C_1$–$C_5$ alkyl optionally containing a terminal —OR''' or —OC(O)R''' moiety wherein R''' is hydrogen or $C_1$–$C_5$ alkyl, (b) —Q wherein Q is a heterocyclic moiety having a labile hydrogen atom so that said moiety acts as a carboxylic acid analogue, (c) —R'X wherein R' is $C_1$–$C_5$ alkyl and X is halogen, (d) —R'C(O)N(R'')$_2$ wherein R' is a direct bond or $C_1$–$C_5$ alkyl and each R'', which may be the same or different, is hydrogen or $C_1$–$C_5$ alkyl optionally containing a terminal —OR''' or —OC(O)R''' moiety wherein R''' is hydrogen or $C_1$–$C_5$ alkyl, (e) —R'-C(O)OR'' wherein R' is a direct bond or $C_1$–$C_5$ alkyl and R'' is hydrogen or $C_1$–$C_5$ alkyl optionally containing a terminal —OR''' or —OC(O)R''' moiety wherein R''' is hydrogen or $C_1$–$C_5$ alkyl, (f) —R' wherein R' is $C_1$–$C_5$ alkyl, or (g) —R'OR''' wherein R' is $C_1$–$C_5$ alkyl and R''' is hydrogen or $C_1$–$C_5$ alkyl, G is halogen, $C_1$–$C_5$ alkyl, or —OR$_2$ wherein $R_2$ is R'', wherein R'' is hydrogen or $C_1$–$C_5$ alkyl optionally containing a terminal —OR''' or —OC(O)R''' moiety wherein R''' is hydrogen or $C_1$–$C_5$ alkyl, —C(O)OR''' wherein R''' is as previously defined, or —C(O)R''' wherein R''' is as previously defined, and $R_3$ is (a) $C_1$–$C_{12}$ alkyl, (b) —OR'''', in which R'''' is a straight chain or branched $C_2$–$C_9$ alkyl which may be substituted at the terminal carbon atom by a phenyl group, or (c) —(CH$_2$)$_n$OR''' wherein n is an integer of 1 to 7 and R''' is hydrogen or $C_1$–$C_5$ alkyl. The compounds according to said formula that are contemplated herein have the (3S,4S) configuration and are essentially free of the (3R,4R) enantiomer.

Certain compounds of the above formula are novel and in themselves constitute an aspect of the present invention. These compounds are those in which $R_1$ is (a) —R'N(R'')$_2$; (b) —Q; (c) —R'X; and (d) —R'-C(O)N(R'')$_2$.

BRIEF DESCRIPTION OF THE DRAWINGS

To assist in the understanding of the invention and, in particular, of the data that is given in the Examples, the following drawing figures are presented herein.

DETAILED DESCRIPTION OF THE INVENTION

COMPOSITIONS AND METHODS OF USE

Figure 1A:
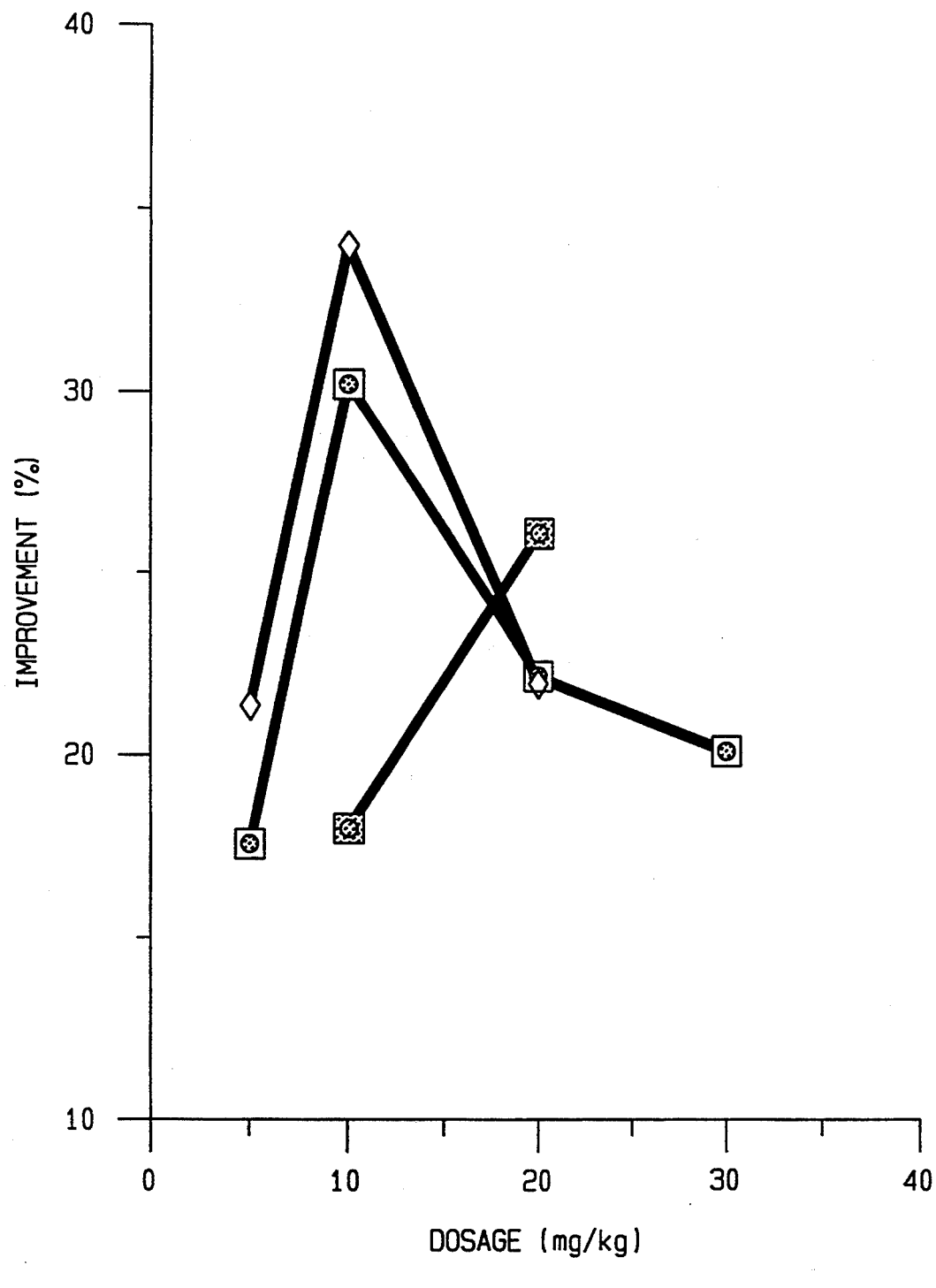
FIG. 1a shows dosage ranges of the compounds HU-254, HU-259, and HU-260 in tests for neuroprotective activity against NMDA toxicity in mice.

The present invention provides novel medicinal uses for the pinene derivatives shown above.

These compounds have unexpectedly been shown to possess neuroprotective effects, that were known previously for certain tricyclic benzopyran compounds of the tetrahydrocannabinol (THC) family. It has now been shown that these bicyclic compounds, which cannot be considered to be classical THC-type compounds, can nevertheless exert beneficial neurological effects. The neuroprotective effects have been evaluated both in vitro and in vivo.

The neuroprotective effects have been corroborated in the following systems:

Binding to the NMDA receptor linked channel: Non competitive antagonists of NMDA, the primary example of which is the compound MK-801, bind to a site within the NMDA receptor channel thus preventing the activation of the receptor-channel complex and the consequent neurotoxicity. The ability of various compounds to compete with the binding of tritium labeled MK-801 to brain membranes is considered a measure of their potency as NMDA non-competitive antagonists.

Blockade of NMDA-induced voltage changes in Xenopus oocytes: Frog oocytes can be injected with genetic material from various species and organs, resulting in the expression of the various molecules encoded by this material in the oocyte. Injection of rat brain RNA provides active NMDA receptors on the ooctye surface. Application of NMDA results in changes in the electrical activity recorded from the oocytes. Various NMDA antagonists block the NMDA-induced changes in electrical activity and their potency and dose dependence in this system indicate their potency and mode of action as NMDA antagonists.

Blockage of NMDA toxicity in tissue culture: Neurons can be grown in culture and survive for several weeks. Application of NMDA to neuronal cultures results in toxicity to the neurons: microscopic viewing of the cultures shows reduced cell density and changes in the shape and staining properties of surviving neurons, and the metabolic activity in the cultures is greatly reduced, as assessed by reduction in the formation of a colored product from chemicals sensitive to the metabolic mitochondrial enzymes. The ability of various compounds to prevent the morphological and metabolic changes induced by NMDA is considered a measure of their neuroprotective activity in culture.

Blockade of NMDA toxicity in mice: Subcutaneous injection of NMDA in mice results in a dose-dependent increase in the number, severity and duration of several neurological symptoms, culminating in death at the higher dose range. The symptoms include tail flicks, circling, tremor and convulsions. The ability of various compounds, when administered to mice prior to NMDA, to reduce the number and severity of these symptoms is a considered a measure of their potency in preventing NMDA behavioral toxicity in vivo.

Protection against hypobaric anoxia in mice: Exposure of mice to a hypobaric (200 mmHg) atmosphere reduces the amount of oxygen available to the animals and results in death within 1–2 minutes in untreated mice. Pretreatment with compounds that can counteract the effects of oxygen deprivation prolong (double or more) the survival time of mice subjected to this treatment. The increase in survival time is a measure of the potency of the compounds in counteracting anoxic damage in vivo.

Inhibition of ischemic neuronal damage in gerbils: Temporary blockage of the blood supply to the gerbil brain by surgical ligation of the two major arteries (common carotids) results in transient global forebrain ischemia. Temporary global ischemia produces a delayed, selective degeneration of neurons in the hippocampus, a brain structure essential for memory formation. The ability of various compounds to prevent hippocampal cell loss and the attendant memory deficits is considered a measure of their potency as neuroprotectants in ischemic conditions.

Each of these systems represents an aspect of neurotoxocity which is amenable to intervention by pharmaceutical agents that bind to the NMDA receptor. It is likely that the compounds of the present invention exert their demonstrated neuroprotective effects by virtue of their ability to bind to the NMDA receptor. Nevertheless, it cannot be ruled out that their activity is mediated by other receptors or additional mechanisms.

The compositions of the present invention are particularly effective in alleviating and even preventing glutamate neurotoxicity due to acute injuries to the central nervous system, such as injuries due to prolonged seizures, compromised or reduced blood supply, deprivation of glucose supply, and mechanical trauma. The present compositions is also effective in alleviating other damage to the CNS, e.g. poison-induced convulsions, considered to be associated with amino acids receptors other than that of glutamate, for example glycine.

The compositions of the present invention are likewise effective in the treatment of certain chronic degenerative diseases which are characterized by gradual selective neuronal loss. In this connection, the compositions of the present invention are contemplated as therapeutically effective in the treatment of Alzheimer's disease.

The present compositions are of special value in grand mal seizures, global hypoxic ischemic insults, in hypoxia, alone or in combination with blood flow reduction (ischemia), as well as in cases of cardiac arrest and in cases of abrupt occlusion of cerebral arteries (stroke).

Thus the present invention provides methods for treatment various pathological conditions including acute injuries to the central nervous system (CNS) associated with excitatory amino acid neurotoxicity, chronic degenerative disease associated with selective neuronal loss, and CNS poisoning.

The compounds are administered for the above defined purposes in conventional pharmaceutical forms, with the required solvents, diluents, excipients, etc. to produce a physiologically acceptable formulation. They can be administered by any of the conventional routes of administration.

Pharmaceutical compositions in which the compounds of the above formula are the active ingredient may be prepared in a variety of forms and dosages. The preparation of such compositions is within the skill of the art. Thus, the compounds may be formulated with a pharmaceutically acceptable diluent or carrier in accordance with standard procedures. For example, a diluent may be chosen that is an aqueous cosolvent solution comprising a pharmaceutically acceptable cosolvent, a micellar solution prepared with natural or synthetic ionic or nonionic surfactants, or a combination of such cosolvent and micellar solutions. A carrier consisting essentially of a solution of ethanol, a surfactant, and water may be used, or a carrier may be selected that consists essentially of an emulsion comprising triglycerides, lecithin, glycerol, an emulsifier, an antioxidant, and water. Prior to their use as medicaments, the pharmaceutical compositions will generally be formulated in unit dosage form. Daily dosages of the compound for humans may range from about 0.1 to about 50 mg/kg, and will preferably be between about 1 and 20 mg/kg.

It will be appreciated that the most appropriate administration of the pharmaceutical compositions of the present invention will depend on the type of injury or disease being treated. Thus, the treatment of acute head trauma, stroke or ischemic brain damage resulting from cardiac arrest will necessitate systemic administration of the drug as rapidly as possible after induction of the injury. On the other hand, diminution or prophylaxis of chronic degenerative damage will necessitate a sustained dosage regimen.

Similar formulation constituents and dosage ranges will apply to pharmaceutical compositions having analgesic, anti-emetic, sedative, anti-inflammatory, anti-glaucoma, or neuroprotective activities which contain as an active ingredient a therapeutically effective quantity of a novel compound as described immediately hereinbelow.

NOVEL COMPOUNDS

The present invention also provides novel compounds of the formula

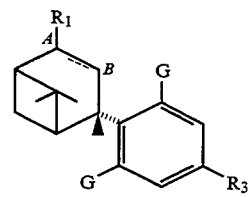

having the (3S,4S) configuration and which is essentially free of the (3R,4R) enantiomer, wherein
the dotted line A - - - B indicates an optional bond,
$R_1$ is
(a) $-R'N(R'')_2$ wherein $R'$ is $C_1$–$C_5$ alkyl and each $R''$, which may be the same or different, is hydrogen or $C_1$–$C_5$ alkyl optionally containing a terminal $-OR'''$ or $-OC(O)R'''$ moiety wherein $R'''$ is hydrogen or $C_1$–$C_5$ alkyl,
(b) $-Q$ wherein Q is a heterocyclic moiety having a labile hydrogen atom so that said moiety acts as a carboxylic acid analogue,
(c) $-R'X$ wherein $R'$ is $C_1$–$C_5$ alkyl and X is halogen,
(d) $-R'C(O)N(R'')_2$ wherein $R'$ is a direct bond or $C_1$–$C_5$ alkyl and each $R''$, which may be the same or different, is hydrogen or $C_1$–$C_5$ alkyl optionally containing a terminal $-OR'''$ or $-OC(O)R'''$ moiety wherein $R'''$ is hydrogen or $C_1$–$C_5$ alkyl, or
(e) $-R'C(O)OR''$ wherein $R'$ is a direct bond or $C_1$–$C_5$ alkyl and $R''$ is hydrogen or $C_1$–$C_5$ alkyl optionally containing a terminal —OR''' or —OC-
(O)R''' moiety wherein R''' is hydrogen or $C_1$-$C_5$
alkyl, G is (a) halogen, (b) $C_1$-$C_5$ alkyl, or (c) —$OR_2$,
wherein $R_2$ is (a') —R'', wherein R'' is hydrogen or
$C_1$-$C_5$ alkyl optionally containing a terminal —OR''' or
—OC(O)R''' wherein R''' is hydrogen or $C_1$-$C_5$ alkyl,
(b') —C(O)OR''' wherein R''' is as previously defined,
or (c') —C(O)R''' wherein R''' is as previously defined,
and $R_3$ is (a) $C_1$-$C_{12}$ alkyl, (b) —OR'''', in which R'''' is a
straight chain or branched $C_2$-$C_9$ alkyl which may be
substituted at the terminal carbon atom by a phenyl
group, or (c) —$(CH_2)_n$OR''' wherein n is an integer of 1
to 7 and R''' is hydrogen or $C_1$-$C_5$ alkyl.

Particularly preferred at present are those compounds of the above formula in which $R_3$ is 1,1-dimethylheptyl or 1,2-dimethylheptyl. It is these embodiments of $R_3$ that are found in THC and its analogues. However, for the neuroprotective activity which characterizes the present invention, it is believed that any lower or mid-range alkyl substituent will be suitable at this position.

Among the preferred subgroups of compounds of the above formula are those wherein Q is a saturated or unsaturated ring of 4 to 8 members consisting of C with at least one of N, S, and O, said ring being optionally substituted with —COR''' or —COOR''' wherein R''' is as previously defined. Most preferably in this embodiment, $R_1$ is tetrazol-5-yl.

Another preferred subgroup is that wherein A - - - B is a covalent bond, $R_1$ is —C(O)N(R'')$_2$ or —C(O)OR'', $R_2$ is —OC(O)R''', and $R_3$ is $C_5$-$C_{12}$ alkyl.

Among the more preferred embodiments of this subgroup when $R_1$ is COOH are the compounds wherein $R_1$ is COOH, $R_2$ is hydrogen or acetyl, and $R_3$ is 1,1-dimethylheptyl or 1,2-dimethylheptyl. The most preferred carboxy compound has the formula

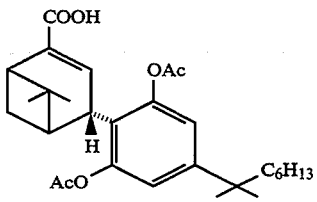

and is referred to herein as HU-259.

There are three classes of more preferred embodiments of the subgroup wherein $R_1$ is a carboxamide.

In one, $R_1$ is an amino acid carboxamide, $R_2$ is acetyl, and $R_3$ is 1,1-dimethylheptyl or 1,2-dimethylheptyl. Most preferred of these is the compound of claim 12 wherein $R_1$ is glycine carboxamide, $R_2$ is acetyl, and $R_3$ is 1,1-dimethylheptyl or 1,2-dimethylheptyl.

In another, $R_1$ is ethanol carboxamide, $R_2$ is acetyl, and $R_3$ is 1,1-dimethylheptyl or 1,2-dimethylheptyl. The most preferred ethanol carboxamide compound has the formula

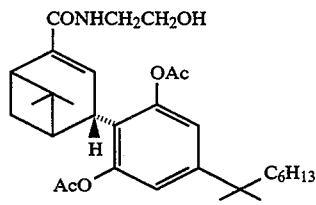

and is
referred to herein as HU-271.

In the third class of more preferred carboxamide derivatives, $R_1$ is diethylcarboxamide, $R_2$ is acetyl, and $R_3$ is 1,1-dimethylheptyl or 1,2-dimethylheptyl. Most preferred of this class is the compound that has the formula

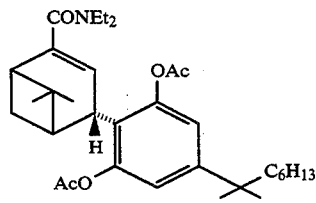

and is referred to herein as HU-270.

The present invention further provides processes for the synthesis of these novel compounds. Compound HU-259 is synthesized according to scheme A. Step a in this scheme has been previously reported (Mechoulam et al., Tetrahedron: Asymmetry 1: 315-319, 1990). Step c represents a selective acetylation leading to the novel compound (HU-260), which in two oxidative steps leads to the central compound of this invention, HU-259. By standard procedures HU-259 can be converted into various amides such as HU-270 and HU-271 which also exhibit the same pharmaceutical profile.

SCHEME A

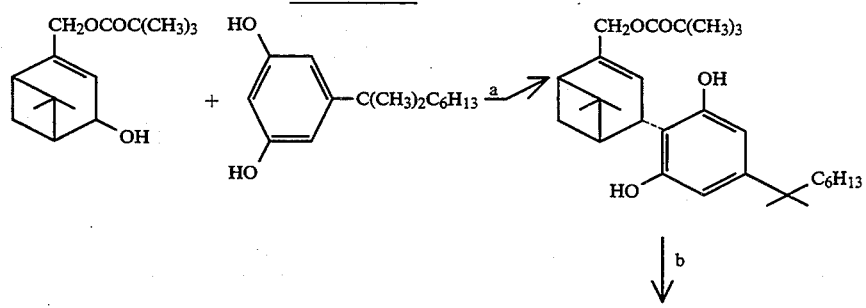

-continued
SCHEME A

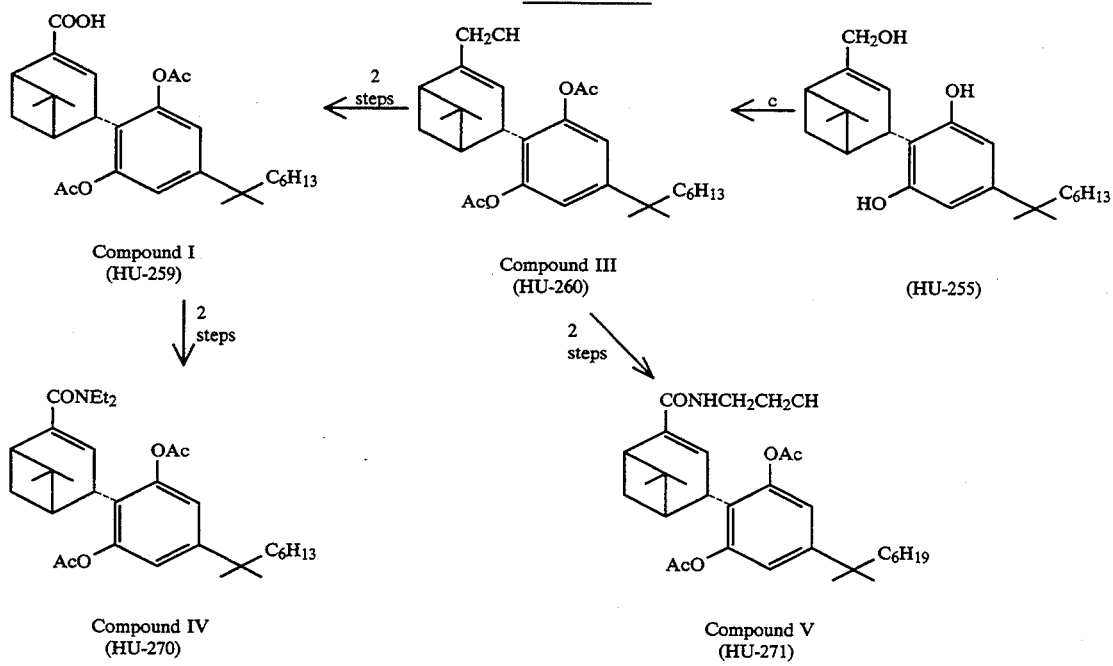

A more direct route to HU-270 is depicted in scheme B.

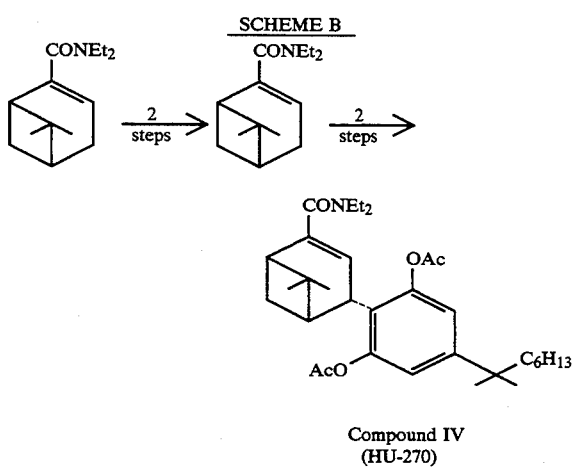

EXAMPLES

The following examples are intended to illustrate the present invention, and these are to be construed in a non-limitative manner. It is clear that various modifications in the process of the invention and in the choice of reactants might be resorted to by one skilled in the art without departing from the scope of the present invention.

A variety of synthetic methods may be employed to prepare compounds according to the present invention. For instance, carboxamides according to the present invention may be prepared by a process that comprises reacting a 4-hydroxy myrtenyl ester with 5-(1,1-dimethyl heptyl) resorcinol, in the presence of anhydrous p-toluene sulfonic acid; de-esterification of the diol product to give the triol; selective esterification of the triol to give the phenyl ester; oxidation of the product to give the aldehyde; oxidation of the aldehyde to give the carboxylic acid; and reaction of the carboxylic acid with the appropriate amine to yield the amide. Likewise, carboxylic acid esters according to the invention may be prepared by a process that comprises reaction of myrtenoic acid with the appropriate amine to yield the amide; oxidation of the amide to yield a 4 ketone derivative; reduction of the ketone to the 4 hydroxy derivative; reaction of the 4 hydroxy compound with a resorcinol derivative in the presence of anhydrous p-toluene sulfonic acid; and esterification of the reaction product. The specific Synthetic Examples that follow will further illustrate the manner in which the novel compounds of the present invention may be prepared.

SYNTHETIC EXAMPLE 1

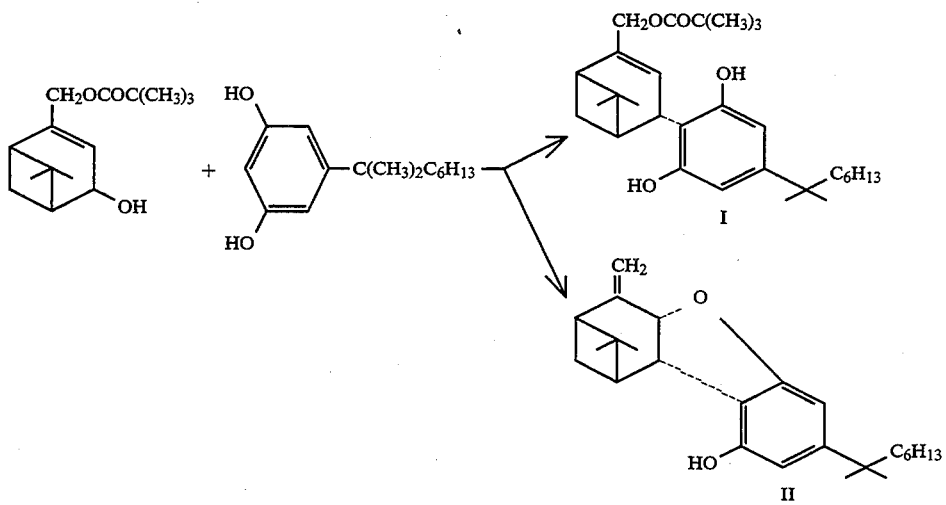

4-Hydroxy-myrtenyl pivalate (1.32 g, 5.24 mmoles) in dry freshly distilled methylene chloride (50 ml) was added, under nitrogen atmosphere, over a period of 30 min to a solution of 5-(1,1-dimethyl heptyl)resorcinol (1.24 g, 5.27 mmoles) and dry anhydrous p-toluene sulfonic acid (270 mg) in dry methylene chloride (200 ml). The solution was left at room temperature for 60 min, washed with a saturated solution of sodium bicarbonate, dried and evaporated. The oil obtained was chromatographed on silica gel with 5% ether in petroleum ether as eluting solvent. The first compound to be eluted was compound II (30 mg) m.p. 154°–155°.

The second compound eluted was compound I, obtained as a semi-solid (1.43 g, 60%).

$[\alpha]_D = 75°$ (EtOH)

I.R. (neat) 1620 cm$^{-1}$

HNMR (CDCl$_3$) δ 0.82, 1.10, 1.18, 1.20, 1.39, 4.09, 4.16, 6.0, 6.21

Compound II was reported by us in J. Med. Chem. 33: 1037 (1990).

Compound I is mentioned in our HU-211 patent (U.S. Pat. No. 4,876,276) and synthetic paper (Tetrahedron: Asymmetry 1: 315 (1990)).

SYNTHETIC EXAMPLE 2

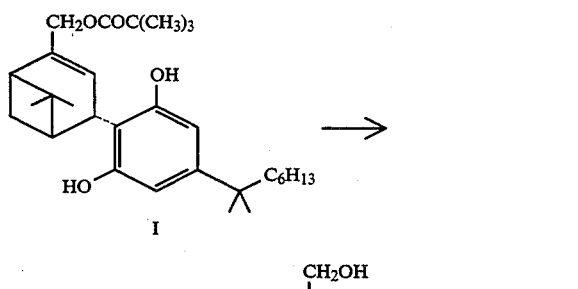

The diol I (4.3 g, 9 mmoles) in dry ether (100 ml) was added to lithium aluminum hydride (850 mg) in dry ether (60 ml) under an N$_2$ atmosphere. The mixture was boiled under reflux for 2 hours. Excess reagent was destroyed with ethyl acetate followed by a saturated aqueous solution of magnesium sulfate. The ether layer was decanted, dried and evaporated. The oil obtained was chromatographed on a silica gel column (70 g). Elution with 25% ether in petroleum ether gave the triol III (2.95 g, 85%) as an unstable solid, which should be used within a day.

SYNTHETIC EXAMPLE 3

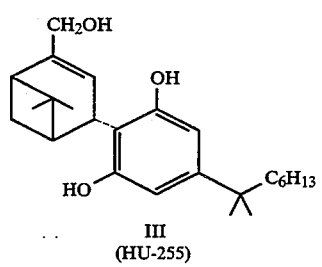

Acetic anhydride (2.5 ml) was added to compound III (0.965 g, 2.5 mmoles) dissolved in pyridine (5 ml). The solution was stirred at room temperature for 24 hours. Water was added and the mixture partitioned between water and ether. The ether layer was washed with 10% hydrochloric acid (to remove pyridine) and water. The organic layer was dried and evaporated. The oil obtained was chromatographed on silica gel column (30 g) using 10% ether in petroleum ether as the eluting solvent. The product IV (1.1 g, 93%) was obtained as an oil.

$[\alpha]_D = +84.2$ (13.3 mg/2 ml CHCl$_3$)

IR max (neat) 1760 cm$^{-1}$

H NMR (CDCl₃) δ 2.06 (3H s C-7 OCO CH₃) 2.29 (6H s OCOCH₃), 3.75 (1H s C-3 H), 4.5 (2H q C-7 H) 5.68 (1H s C-2 H), 6.83 (2H s arom).

SYNTHETIC EXAMPLE 4

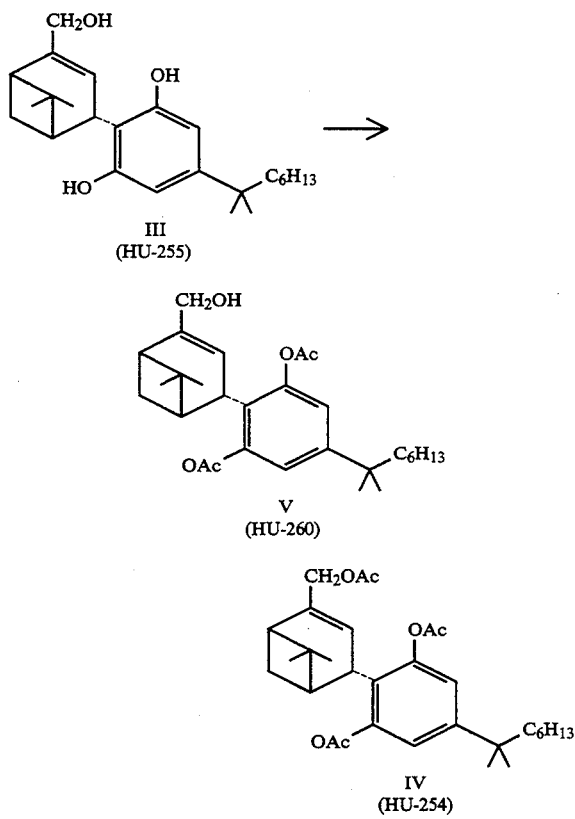

III
(HU-255)

V
(HU-260)

IV
(HU-254)

The acetylation follows the procedure described by C. G. Pitt et al. (using a different base).*

*C. G. Pitt, M. S. Fowler, S. Sathe, S. C. Srivastava and D. L. Williams, J. Amer. Chem. Soc. 97: 3798 (1975).

Potassium 2-methyl butoxide** (35 ml of 0.55M; 19 mmoles) in benzene was added to the triol III (3.33 g, 8.63 mmoles), protected from light, in dry benzene (300 ml). The solution was stirred for 1 h, when acetic anhydride (1.78 ml, 19 mmoles) was added. After 3 h, the mixture was acidified with 10% hydrochloric acid. The organic layer was washed with aqueous sodium bicarbonate and water, dried and evaporated. The oil obtained was chromatographed on a silica gel column (180 g). The first eluted compound (220 mg, 5%. Using 5% ether in petroleum ether as the eluting solvent) was found to be identical with the triacetate IV. The second eluted compound (using 20% ether in petroleum ether as eluting solvent) compound V (2.97 g, 73.2%) was obtained as an oil.

**Reaction may be carried out using commercial potassium tert-butoxide solution in THF. Yield of V circa 50%.

[α]$_D$ = +48° (7.5 mg/2ml CHCl₃).

IR λ max (neat) 3400 (OH), 1780 (OAC) cm$^{-1}$

IH NMR (CDCl₃), δ 2.23 (OH s OCOCH₃), 3.75 (1H s C-3 H) 4.06 (2H s C-7 H), 5.6 (1H s C-2 H), 6.829 (2H arom)

SYNTHETIC EXAMPLE 5

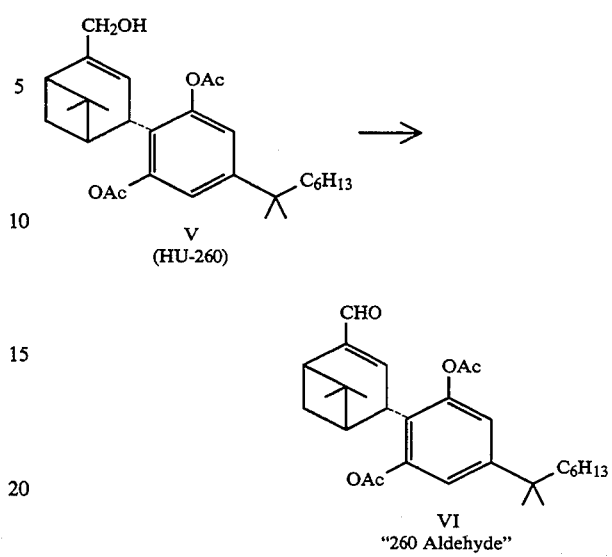

V
(HU-260)

VI
"260 Aldehyde"

This oxidation follows the procedure described by Corey and Samuelson*. Dry pyridine (1.97 ml) followed by chromic oxide (1.27 g, 12.7 mmoles) was added to a solution of methylene chloride-DMF (4:1) (30.5 ml). The mixture was stirred for 15 min. The allylic hydroxy compound V (1.44 g, 3.06 mmoles) in methylene chloride-DMF (4:1) (6 ml) was added and the reaction mixture stirred at room temperature for 2 hours. Ethanol (1.6 ml) was added, and the mixture stirred for an additional 10 min. and then diluted with ethyl acetate (160 ml). The resulting mixture was filtered through a sintered-glass funnel, packed with silica (3 cm), with a layer of anhydrous sodium sulfate on top, and eluted with ethyl acetate (500 ml). The ethyl acetate filtrate was washed with dilute hydrochloric acid (1N) and then with sodium bicarbonate solution and water. After evaporation of the dried organic solvent, oil was obtained. This oil was purified on a silica gel column (60 g. Elution with 10% ether in petroleum ether) to give pure aldehyde VI (22 g, 85%) as an oil.

*Corey, E. S., Samuelsson, B. One-step conversion of primary alcohols in the carbohydrate series to the corresponding carboxylic tert-butyl esters. J. Org. Chem. 49: 47-35 (1984).

[α]$_D$=49° (8.2 mg/2 ml CHCl₃)

IR λ max (neat) 1680, 1780 cm$^{-1}$-1 H NMR, δ 2.2 (6H s OCOCH₃), 3.98 (1H C-3 H), 6.82 (1H C-2 H), 6.88 (2H s arom), 9.55 (1H s C-7 H).

SYNTHETIC EXAMPLE 6

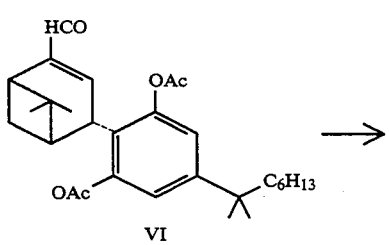

VI

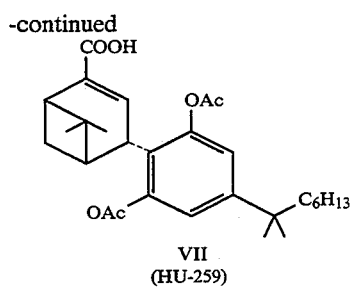

This oxidation follows the procedure described by Pellegata et al.*

*Pellegata, R., Ventura, P., Villa, M., Palmisano, G., Lesma, G. An improved procedure for the synthesis of oleuropeic acid. Synt. Commun. 15: 165 (1985).

This procedure is based on publications by B. O. Lindgren and Nilsson (Acta Chem. Scand. 27: 888, 1973), Corey and Myers (J. Amer. Chem. Soc. 107: 5574, 1985) and Corey and Reichard (J. Amer. Chem. Soc. 114: 10677, 1992).

Sodium chlorite (990 mg) was added portionwise with vigorous stirring to the aldehyde VI (0.95 g, 2.03 mmoles), 2-methyl-2-butene (4.55 ml), saturated aqueous potassium dihydrogen phosphate (2.7 ml) and tert-butyl alcohol (45 ml). The reaction mixture was stirred at room temperature for 5 h. Water (40 ml) was added and the mixture extracted several times with ethyl acetate, dried and evaporated to give the crude acid which was purified on a silica gel column (12 g) (elution with 20% ether in petroleum ether) to give the acid VII (0.78 g, 80%) as an amorphous solid.

$[\alpha]_D = 89$ (11.2 mg/ml CHCl$_3$)

IR $\lambda$ max (neat) Broad band in the 2800–3600 cm$^{-1}$ region, 1780, 1690 cm$^{-1}$ H NMR (CDCl$_3$) $\delta$ 2.2 (6H s OCOCH$_3$), 3.85 (1H s C-3 H), 6.88 (2H s atom), 7.18 (1H sC-2 H).

SYNTHETIC EXAMPLE 7

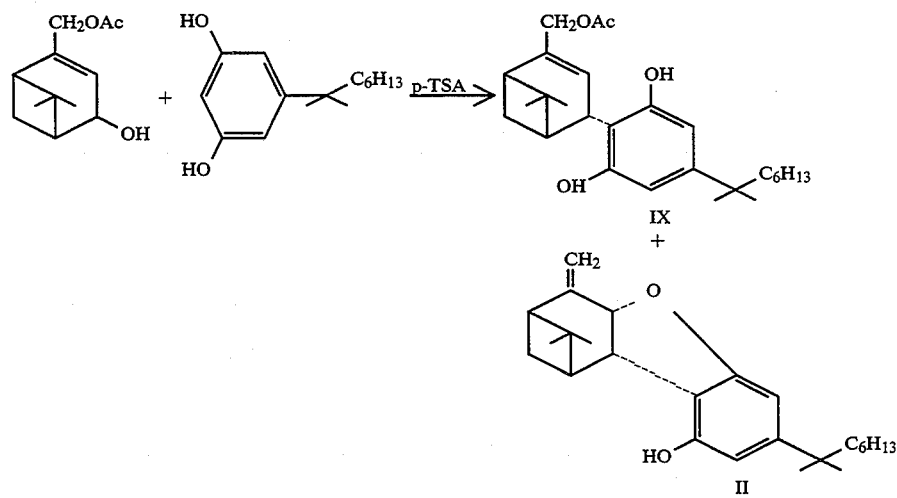

4-Hydroxy myrtenyl acetate (1.2 g, 5.7 mmoles) in dry freshly distilled methylene chloride (50 ml) was added, under nitrogen atmosphere, over a period of 30 minutes, to a solution of 5-(1,1-dimethyl heptyl) resorcinol (1.3 g, 5.5 mmoles) and dry p-toluene sulfonic acid (300 mg) in dry methylene-chloride (200 ml). The solution was stirred at room temperature for 2 hours, washed with a saturated solution of sodium bicarbonate dried and evaporated. The oil obtained was chromatographed on a silica gel column (100 g) and eluted with 5% ether:petroleum ether solution. Compound II (330 mg) followed by compound IX 1.48 g, 60%) were obtained. Compound IX, $[\alpha]_D$ 80° (10 mg/2 ml in C$_2$H$_5$OH).M.S., M+ =428

Footnote

Myrtenyl acetate was prepared from myrtenol and acetic anhydide in pyridine by the usual acetylation method.

Oxo myrtenyl acetate was prepared following the procedure for the preparation of oxo-myrtenyl pivalate.

4-Hydroxy myrtenyl acetate was prepared following the procedure for the preparation of 4-hydroxy myrtenyl pivalate.

SYNTHETIC EXAMPLE 7

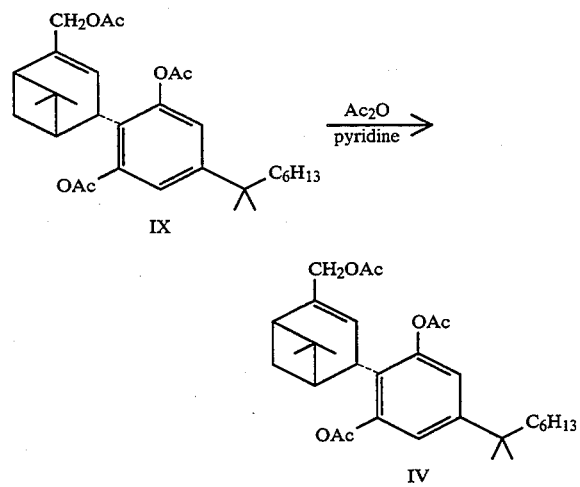

The triacetate was prepared following the usual acetylation method. The triol III was obtained from either IX or IV according to the procedure described in Ex. 2.

The triacetate was prepared following the usual acetylation method.

The triol III was obtained from either IX or IV according to the procedure described in Example 2.

SYNTHETIC EXAMPLE 8

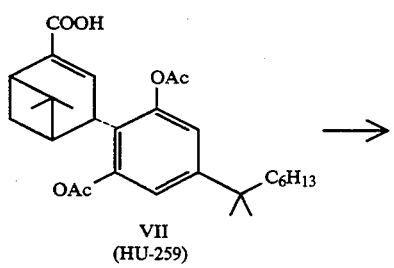

VII
(HU-259)

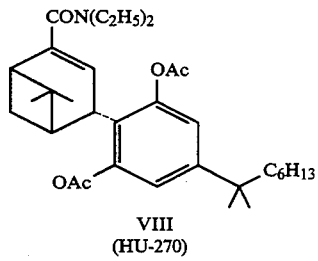

VIII
(HU-270)

To the acid VII (209 g, 0.433 mmoles) dissolved in dichloromethane (2 ml) was added dimethylformamide (0.038 ml) followed by the slow addition of oxalylchloride (0.43 ml of 2M solution in dichloromethane). The reaction was stirred, under nitrogen atmosphere at room temperature for 1 hour, and then evaporated to give the chloride of VII. The chloride was dissolved in dichloromethane (2 ml) and added slowly to a cold solution of diethylamine (0.46 ml, 43 mmoles) in dichloromethane (1 ml). The mixture was stirred at 0° C. for 30 min, washed with 10% hydrochloric acid (to remove the diethylamine) and water. After evaporation of the dry solution the amide VIII (200 mg, 97%) was obtained as an oil.

$[\alpha]_D = +88.5$ (12.8 mg/2 ml CHCl$_3$)
I.R. max (neat) 1760 cm$^{-1}$
H NMR (CDCl$_3$) δ 2.28 (6H s OCOCH$_3$), 3.4 (4H b N-CH$_2$), 3.89 (1H s C-3 H), 5.9 (1H s C-2 H), 6.85 (2H s arom).

SYNTHETIC EXAMPLE 9

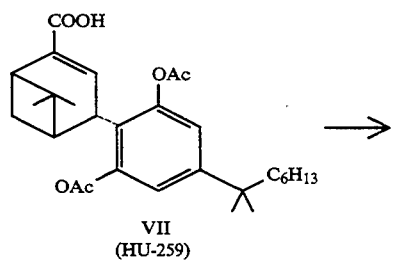

VII
(HU-259)

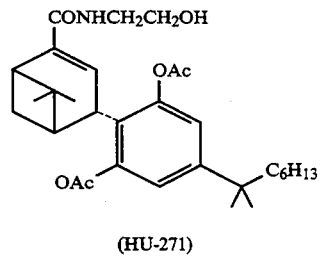

(HU-271)

The acid chloride of HU-259 was prepared following the procedure described in Example 8.

The acid chloride (0.2 mmoles) was dissolved in dichloromethane (1.5 ml) and added slowly to a cold solution of ethanolamine (0.1 ml) in dichloromethane (1 ml). The mixture was stirred at 0° C. for 30 min, washed with water dried and evaporated to give the amide HU-271 as a single compound.

$[\alpha]_D = 48°$ (C=11.2 mg/2 ml CHCl$_3$)
I.R. max (neat) 3300 (OH), 1780 cm$^{-1}$
H NMR (CDCl$_3$), δ 2.26 (6H s OCOCH$_3$), 3.45 (2H b N-CH$_2$), 3.72 (2H CH$_2$OH), 3.79 ( 1H s C-3 H), 6.35 ( 1H C-2 H), 6.43 (1H NH), 6.85 (2H s arom).

Scheme B

SYNTHETIC EXAMPLE 10

Synthesis of HU-271 according to Scheme B. Step 1 oxidation of myrtenol to myrtenoic acid.

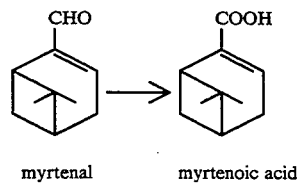

myrtenal     myrtenoic acid

This oxidation follows the procedure described by Pellegata et al.*

*Pellegata, R., Ventura, P., Villa, M., Palmisano, G., Lesma, G. An improved procedure for the synthesis of oleuropic acid. Synt. Commun. 15: 165 (1985).

Sodium chlorite (15.6 g) was added portionwise with vigorous stirring to myrtenol (4.9 g, 32 mmoles), 2-methyl-2-butene (74 ml), saturated aqueous potassium dihydrogen phosphate (44 ml) and tert-butyl alcohol (500 ml). The reaction mixture was stirred at room temperature overnight. Water (600 ml) was added and the mixture was extracted several times with ethyl acetate, dried and evaporated to give myrtenoic acid (100%) as an oil. This oil was used with no further purification.

I.R. λ max (neat): Broad band in the 2800–3400 cm$^{-1}$ region, 1680 cm$^{-1}$.

1H NMR (CDCl$_3$) δ 0.87, 1.35 (CH$_3$) 2.15–2.79 (C-1 H C-6 H), 7.01 (1H C-3 H)

SYNTHETIC EXAMPLE 10

Step 2 Amidation of myrtenoic acid with diethylamine.

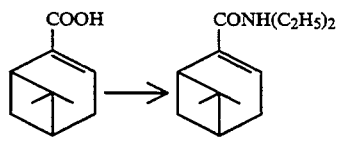

To a solution of myrtenoic acid (440 mg, 2.65 mmole) in dry methylene chloride (5 ml) and dimethylformamide (0,212 ml, 2.65 mmoles), was added a 2M solution of oxalyl chloride in methylene chloride (2.65 ml, 5.3 mmoles). The resulting solution was stirred, at room temperature under a nitrogen atmosphere, for two hours and evaporated to dryness. The acid chloride thus obtained was dissolved in methylene chloride (5 ml) and added slowly to a cold solution (ice bath) of diethylamine (1.4 ml, 13.25 mmoles) in methylene chloride (4 ml).

The reaction was stirred at 0° C. for 30 min, washed to neutral, dried over magnesium sulfate and evaporated to give oil (585 mg). This oil was further purified on 10 g silicon gel chromatography, using 20% ether in petroleum ether as eluent, to give the pure amide (550 mg, 94%).

I.R. λ max (neat): 1610 cm$^{-1}$

1H NMR (CDCl$_3$); δ 3.4 m (4H N-CH$_2$), 5.73 (1H C-3 H).

SYNTHETIC EXAMPLE 10
Step 3 Oxidation of myrtenoic acid diethylamide

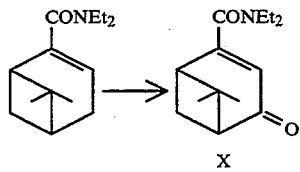

The oxidation follows the procedure described by J. Muzart*.

*Jacques Muzart, Tetrahedron Lett. 28: 4665 (1987).

To an ice-cold solution of chromium (VI) oxide (0.764 g, 7.64 mmoles) in acetonitrile (30 ml) was added 70% tert-Butylhydroperoxide (14 ml, 106.4 mmoles) followed by the immediate addition of a solution of the amide (3.37 g, 15.2 mmoles) in acetonitrile (20 ml). The mixture was stirred at room temperature for 1 hour, diluted with ether and washed with freshly prepared 10% solution of sodium sulfite (130 ml). The organic layer was dried and evaporated to dryness. The oil obtained was chromatographed on a silica gel column (150 g). Elution with 40% ether in petroleum ether gave the ketone (X) (1.16 g, 32%) as an oil.

I.R. λ max (neat): 1680, 1620 cm$^{-1}$

1H NMR (CDCl$_3$); δ 2.24 d (1H C-5 H), 5.85 (1H C-3 H)

SYNTHETIC EXAMPLE 10
Step 4 Reduction of the ketone to the hydroxyl

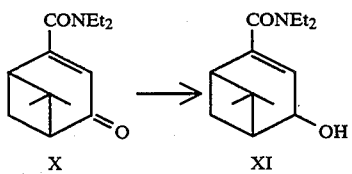

To the ketone (XI) (358 mg, 1.5 mmoles) in ethanol (3 ml) was added, in portion, sodium borohydride (80 mg, 2.1 mmoles). The mixture was stirred at room temperature for 45 min, and was then partitioned between ether and water. The organic layer was dried over magnesium sulfate and evaporated to give compound (XI) (344 mg, 97%) as an oil.

I.R. λ max (neat): 3400, 1610 cm$^{-1}$

1H NMR (CDCl$_3$); δ 4.58 (1H C-4 H), 5.80 (1H C-3 H).

SYNTHETIC EXAMPLE 10
Step 5 Reaction of myrtenoic amide with resorcinol

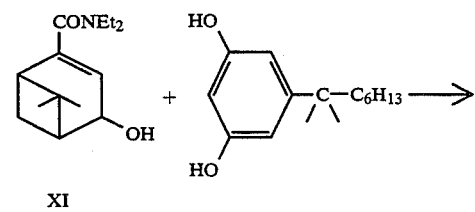

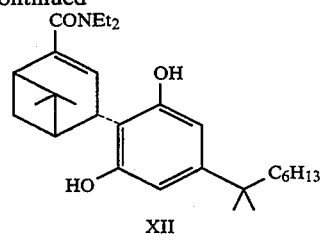

Compound (XI) (620 mg, 2.62 mmoles) in dry methylene chloride (13 ml) was added to a solution of 5-(1,1 dimethyl heptyl)-resorcinol (625 mg, 2.65 mmoles) and dry p-toluene sulfonic acid (126 mg) in dry methylene chloride (30 ml). The solution was left at room temperature, under a nitrogen atmosphere, for 72 hours and then refluxed for 3 hours. The resulting reaction mixture was washed with a saturated solution of sodium bicarbonate, dried and evaporated. The oil obtained was chromatographed on a silica gel column (50 g) with 25% ether in petroleum ether as eluting solvent. Compound (XIII) (350 mg, 30%)* m.p. 146–148 (pentane) was obtained.

*Jacques Muzart, Tetrahedron Lett. 28: 4665 (1987).

1H NMR (CDCl$_3$); δ 4.1 (1H C-3 H), 5.3 (1H C-2 H), 6.285 (2 H aromatic).

SYNTHETIC EXAMPLE 10
Step 6

The acetate (VIII) was prepared from compound (XII) and acetic anhydride in pyridine by the usual acetylation method. The I.R. NMR and Rf values of compound (VIII) were found to be identical with those of compound HU-270.

I.R. λ max (neat): 2850, 1780, 1600 cm$^{-1}$

1H NMR (CDCl$_3$); δ 3.4 (4H N-CH$_2$), 3.86 (1H C-3 H), 5.85 (1H C-2 H), 6.83s (2H arom.).

PHARMACOLOGICAL EXAMPLES

The Drawings

Neuroprotective activity of HU-254, HU-259, and HU-260

FIG. 1a shows dose range in mice pretreated with test compounds and exposed to NMDA toxicity (60 mg/kg s.c.). Test drugs were administered intraperitoneally at the stipulated doses in a solution of MCT oil.

Each point represents the mean scores of eight mice treated with the drug compared to the same number of control animals receiving the vehicle alone.

Figure 1B:
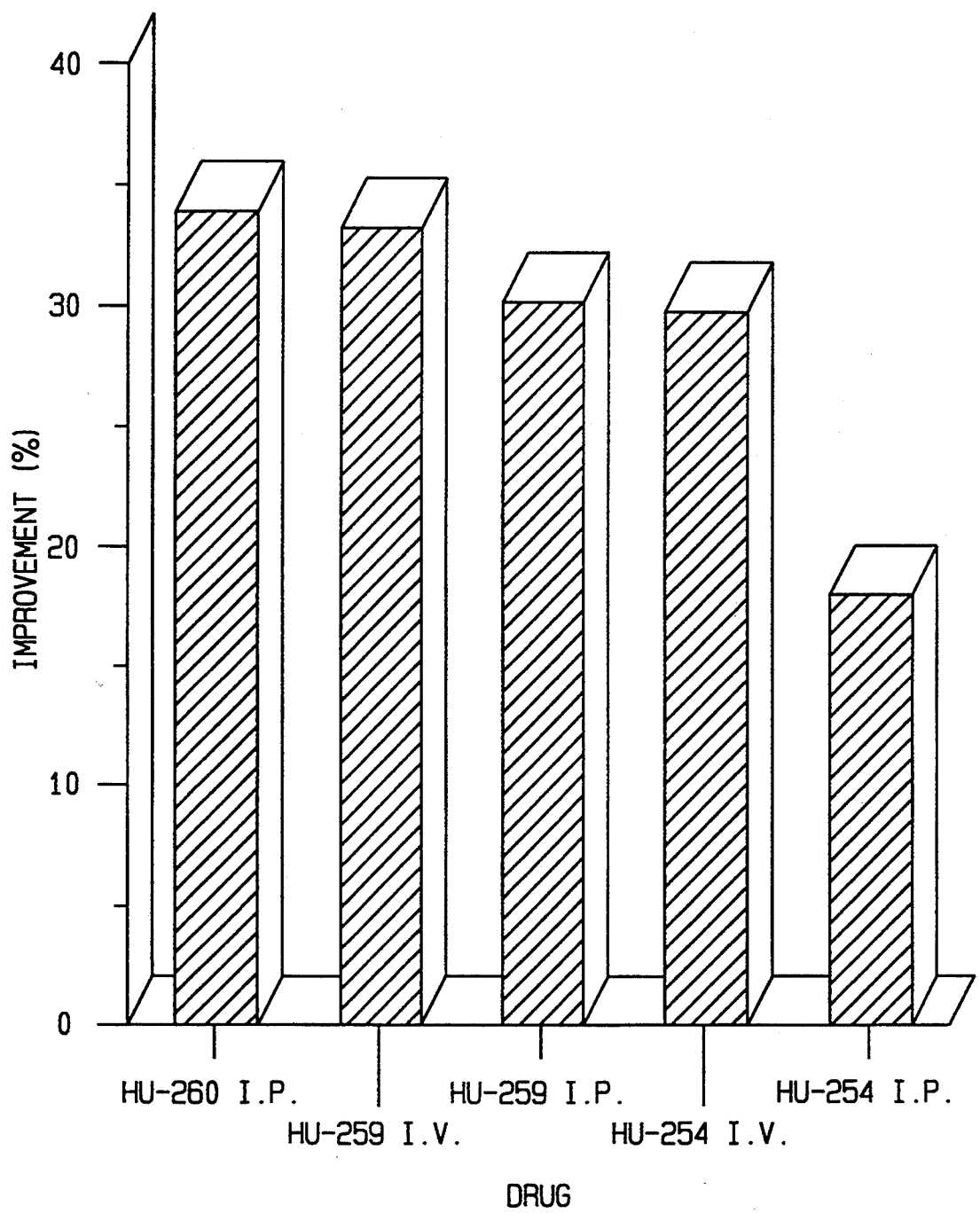
FIG. 1b illustrates the improvement in neurological scores in mice pretreated with test compounds (HU-254, HU-259, HU-260) and exposed to NMDA toxicity.

FIG. 1b shows improvement in neurological scores in mice pretreated with test compounds and exposed to NMDA toxicity. Test compounds were administered at a standard dose of 10 mg/kg either intraperitoneally (in MCT oil) or intravenously (in a submicronized emulsion).

Neuroprotective activity of HU-270 and HU-271

Figure 2A:
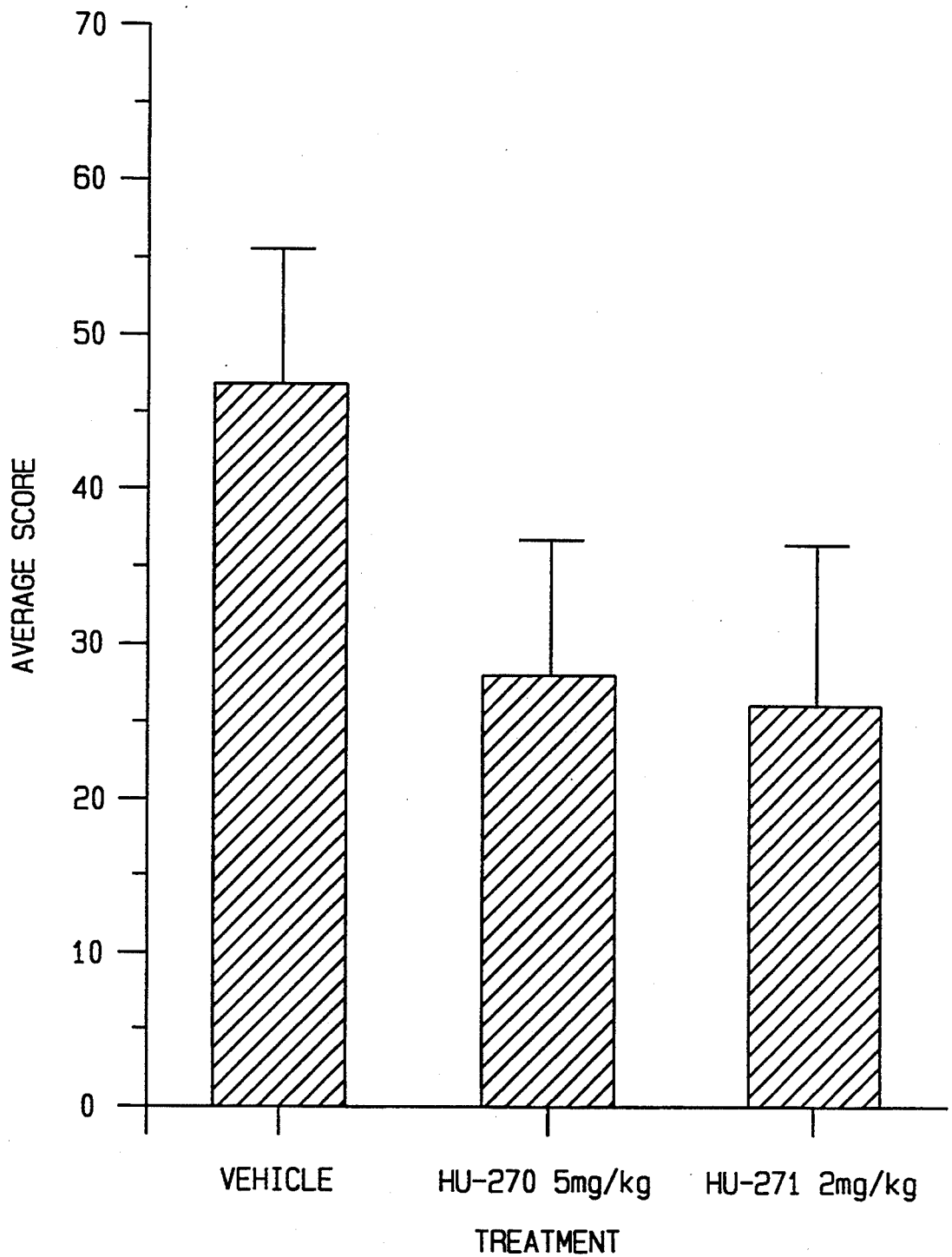
FIG. 2a indicates decreased neurological symptoms in mice pretreated with compounds HU-270 and HU-271 and subsequently exposed to NMDA toxicity.

FIG. 2a shows decreased neurological symptoms in mice pretreated with test drugs and subsequently exposed to NMDA toxicity.

Figure 2B:
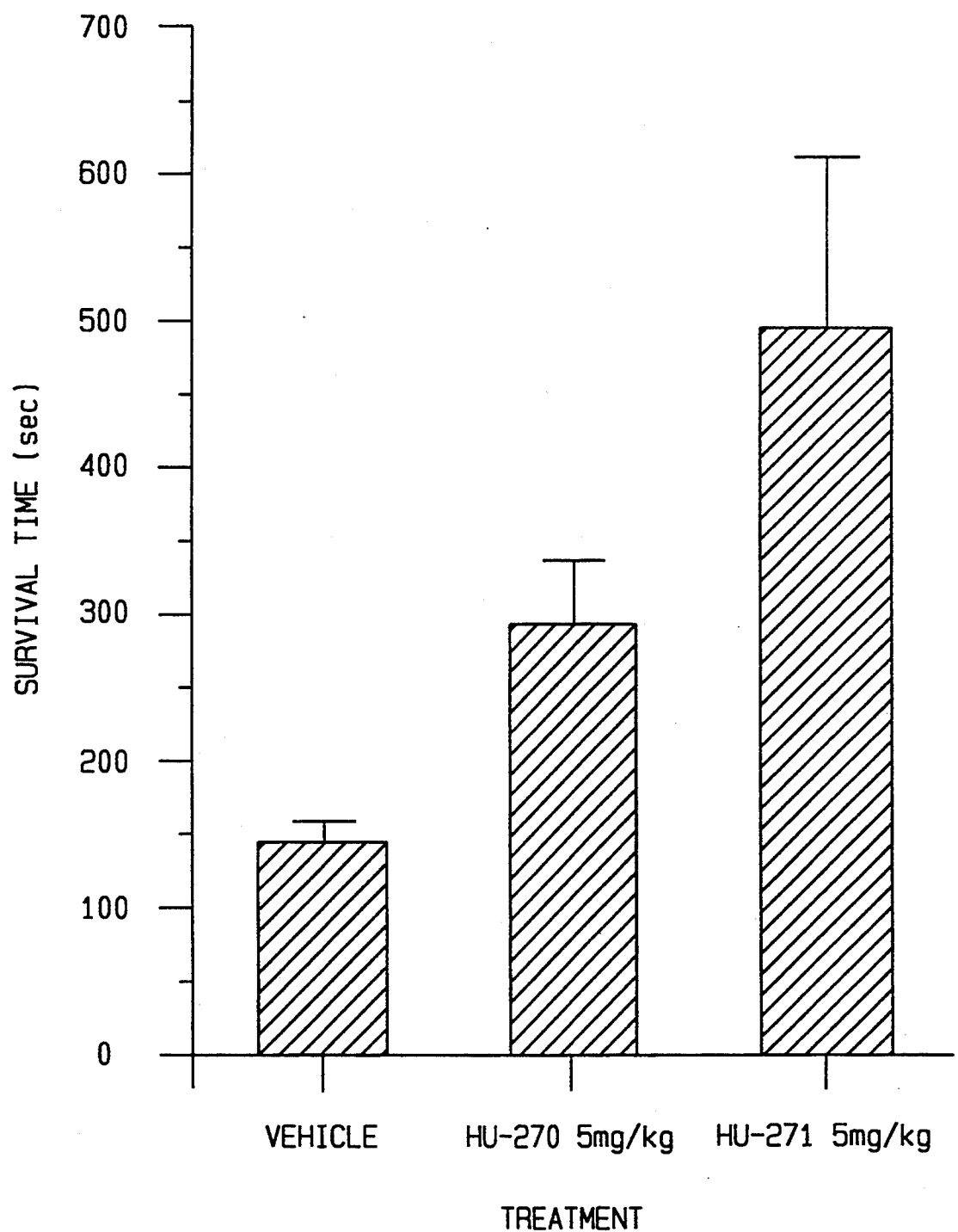
FIG. 2b demonstrates increased survival in mice pretreated with test compounds (HU-270, HU-271) and exposed to hypobaric anoxia.

FIG. 2b shows increased survival in mice pretreated with test drugs and exposed to hypobaric anoxia.

Figure 3:
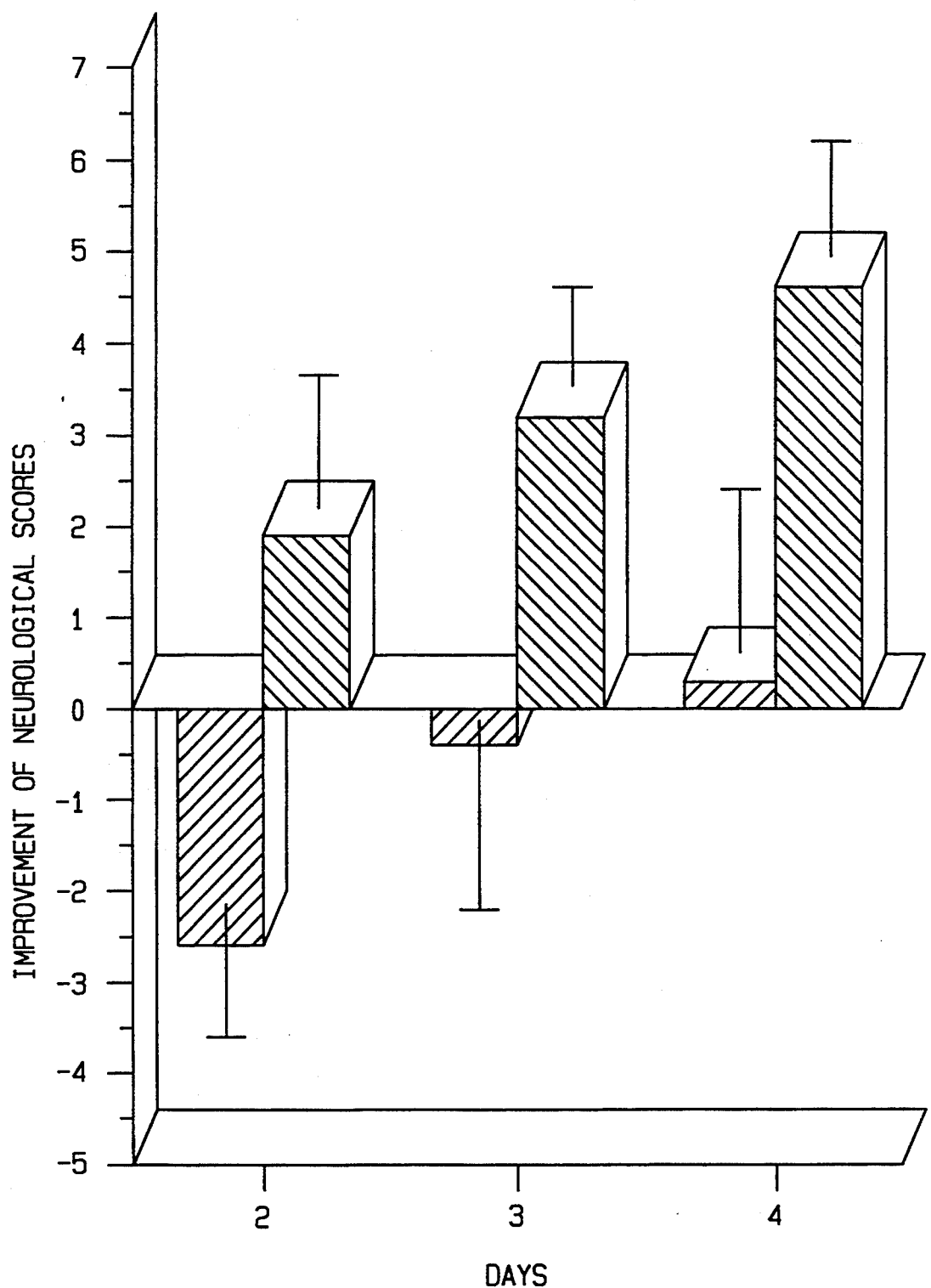
FIG. 3 shows improvement in neurobehavioral scores in gerbils treated with HU-259 after bilateral common carotid artery occlusion.

FIG. 3 shows improvement in neurobehavioral scores in gerbils treated with HU-259 after bilateral common carotid artery occlusion. The data are presented as average differential scores between the initial score obtained 5 hrs post-ischemia and that obtained on each successive day. The drug was administered intravenously 30 min post-ischemia.

Figure 4:
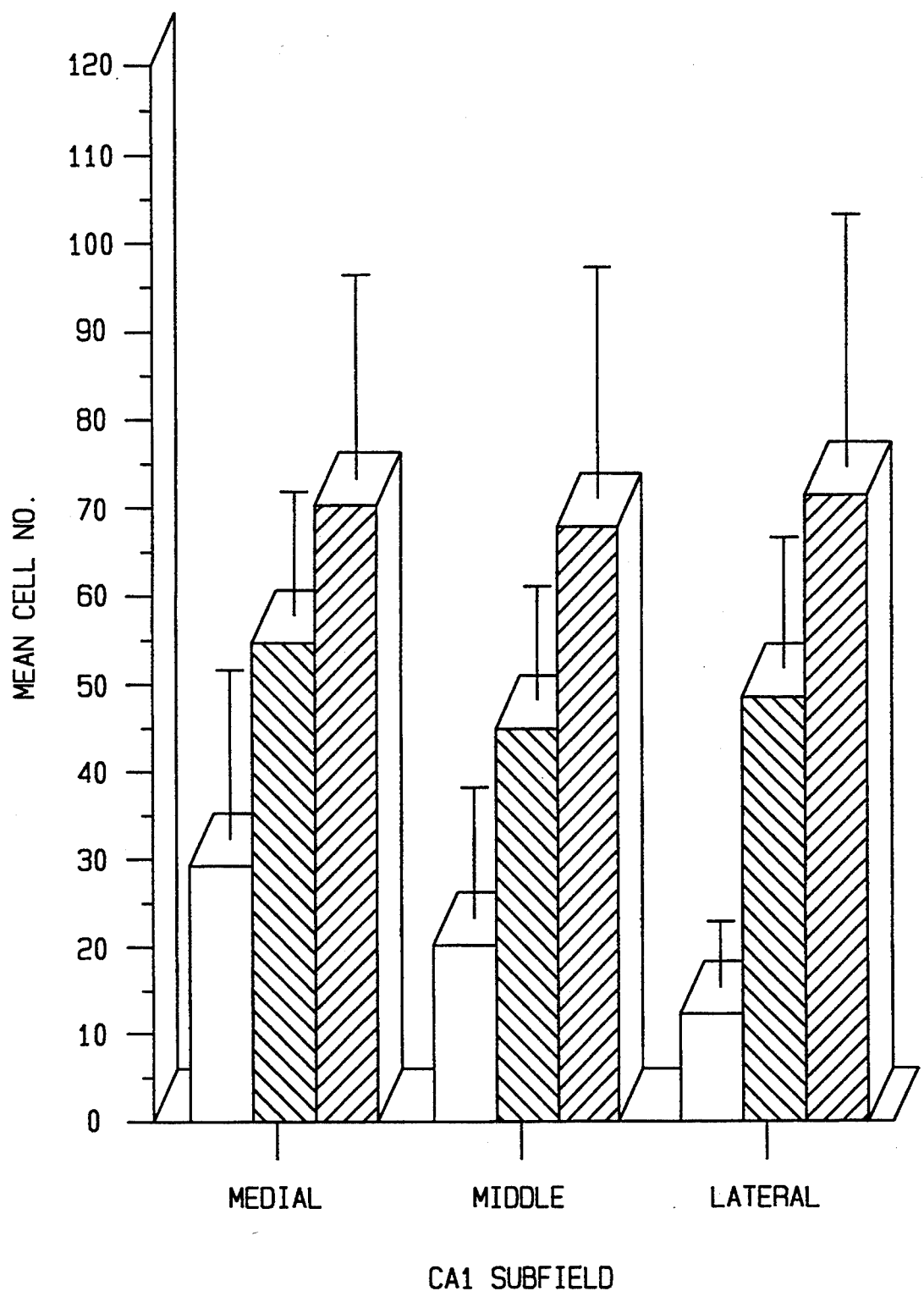
FIG. 4 indicates increased survival of hippocampal cells in ischemic gerbils treated with HU-270 and HU-271 after bilateral common carotid artery occlusion.

FIG. 4 shows increased survival of hippocampal cells of ischemic gerbils treated with HU-270 and HU-271 administered 30 min after bilateral common carotid artery occlusion.

PHARMACOLOGICAL EXAMPLE 11

Antiglaucoma effects of novel 4 phenyl pinene derivative

The synthetic non-psychotropic THC analog, HU-211, has been shown to retain some of the therapeutic activity of naturally occurring THCs including lowering of intraocular pressure (IOP). Bicyclic compounds of the present invention were also tested for IOP lowering effects.

HU-259 is very lipophilic and therefore was formulated in a submicronized emulsion for pharmacological testing, as described for instance by Muchtar et al., *Ophthalmic Res.*, 24, 142–149 (1992) and Benita et al., *J. Pharm. Sci.*, 82, 1069–1079 (1993).

The phospholipids and HU-259 were dissolved in the stabilized oily phase. The other excipients were dissolved in the aqueous phase. Both phases were heated separately to 70° C. and dispersed by a magnetic stirrer. Emulsification was completed using a "high speed mixer" for 5 min at 85° C. The resulting emulsion was cooled rapidly below 20° C. and homogenized using a two-stage homogenizing valve assembly (Gaulin Homogenizer, APV Gaulin, Hilversum, The Netherlands) for 5 min. All the manufacturing procedures were carried out under aseptic conditions and a nitrogen atmosphere. The pH was adjusted to 7.4 using a sodium hydroxide solution (10%). The final fine emulsion was filtered to achieve sterility and stored in ampoules. A typical formulation (%, w/w) consisted of the following: HU-259, 0.2%; oily phase, 20.0%; purified fractionated egg phospholipids, 1.2%; nonionic emulsifier, 2%; glycerin, 2.25%; α-tocopherol, 0.02%; methyl and butyl p-hydroxy- benzoic ester, 0.3 and 0.075%, respectively; and water for injection, to 100.0 g. The control emulsion vehicle was prepared using identical experimental conditions but without drug.

IOP was measured by using a pneumatonometer (Digilab T30). Pressure readings were calibrated for verification every 6 h. One drop (50 μl) of local anesthetic (Benoxinate HCl, 0.4% Fischer [Isr] diluted 1:3 with sterile saline) was instilled into each eye prior to IOP measurements.

A single dose (30 microliter of HU-259 in emulsion (0.2%) was applied to the right eye in three groups of Albino rabbits. IOP was measured for a seven-hour period post-treatment. HU-259 application caused a statistically significant reduction in IOP compared to vehicle controls for over five hours; maximal ocular hypotensive effect was noted at 3 h post-application. Pressure dropped by 3.2±0.7 mmHg (P<0.01) (Table 1). At 7 hours post-treatment, the pressure returned to baseline level. A single dose application lowered the contralateral eye pressure by 2.5±0.9 mmHg due to systemic absorption of the drug. These results suggest that the new synthetic compound, HU-259, in emulsion, is a potent ocular hypotensive drug and indicated a possible therapeutic use of HU-259 in glaucoma.

TABLE 1

| Ocular hypotensive activity of KU-259 in the albino rabbit, compared vith blank vehicle and HU-211 | | | |
|---|---|---|---|
| Group | Eye | Max ΔIOP mmHg | AUC* mmHg × hrs |
| Vehicle | Treated | −0.8 ± 0.7 | −3.9 ± 6.3 |
|  | Contralateral | −0.2 ± 0.8 | −2.8 ± 9.4 |
| HU-259 | Treated | −3.2 ± 0.7** | −10.9 ± 10.9 |
|  | Contralateral | −2.5 ± 0.9** | −7.8 ± 8.1 |
| KU-211 | Treated | −2.9 ± 0.7** | −9.5 ± 6.0 |
|  | Contralateral | −2.0 ± 1.1** | −4.9 ± 7.0 |

*Area Under the Curve from instillation of treatment until return to baseline IOP.
**Drug vs. vehicle P < 0.01.

The mechanism of action of these novel compounds in reduction of IOP is unknown but is not considered to be mediated by their NMDA blocking activity. It is probable that their IOP lowering activity is mediated by other receptors, e.g. muscarinic receptors.

The anti-glaucoma activity of the novel compounds of the present invention provides evidence for their pleitropic neuromodulatory activity which could be relevant to their applicability to chronic neurodegenerative diseases. Furthermore, chronic ischemic damage such as glaucomatous optic neuropathy may be prevented by the dual action of the compound as IOP lowering agent and neuroprotective agent.

PHARMACOLOGICAL EXAMPLE 12

Blockade of NMDA voltage changes in Xenopus expression system.

The oocyte is the most widely used system for studying the molecular, biophysical and pharmacological properties of expressed voltage- or transmitter-operated ion channels. This giant cell offers several advantages for this type of studies. It can be readily used for two-electrode voltage clamp studies, translates injected mRNA from different sources and functionally expresses the translated proteins, and it is also readily amenable for intracellular micron injections. Importantly, the recordings of neurotransmitter- or voltage-induced currents in a single oocyte are extremely stable and can performed repeatedly for 2–3 hours; this allows the performance of a full dose-response relation in single oocytes.

Neuronal receptors for excitatory amino acid (EAA) are becoming increasingly important for the understanding of normal and pathological brain function. Quantitative pharmacological studies of EAA receptor-/ion channel complex are difficult to study in neurons. Therefore, Xenopus oocytes injected with brain mRNA is now the preparation of choice.

Rat brain NMDA receptors were expressed in Xenopus oocytes injected with total rat brain RNA. Dascal and Lotan. The conditions for injection culture and electrical recording from oocytes were as described by Dascal and Lotan (in: Methods in Molecular Biology, Longstaff and Revest, eds. Vol. 13, Chapter 13, Humana Press, N.J., 1992).

Briefly, female Xenopus were anesthetized by immersion in water containing 0.15% tricaine methanesulfonate and a small incision was made in the lower abdomen. Ovary fragments were removed into ND-96.

The oocytes were defolliculated by the collagenase treatment in order to remove the follicle cell layer. Defolliculated oocytes were injected with total rat brain RNA and incubated for 2–4 days at 22° C. in sterile NDE-96 solution. ND-96 solution contains (in mM): NaCl - 96, KCl - 2, $CaCl_2$ - 1.8, Hepes - 5 (pH=7.4–7.6). NDE-96 contains in addition, 2.5 mM sodium pyruvate, 100 unit/ml penicillin, 100 μg/ml streptomycin. A single oocyte was placed in a 1 ml bath constantly superfused with ND-96 solution at room temperature. The cell was impaled with two microelectrodes and held at membrane potential of −60 mV using voltage clamp circuit.

RNA was extracted from the brain of 14-day old rat brain. Each oocyte was injected with 50 nl total RNA (4–8 mg/ml in water, stored at −80° C. in 3–10 nl aliquots).

Oocytes injected with rat brain RNA became responsive to all EAA (NMDA, kainate, glutamate) and to other transmitters (5HT, GABA, etc.). The conductance activated by NMDA was examined more closely.

NMDA receptors were activated by application of NMDA with glycine in Mg-free ND-96 solution. It was shown previously and also observed in this study that the entry of calcium ions through the NMDA receptor-channel evokes a Ca-dependent $Cl^-$ current which appeared as an early inward current peak preceding and overlapping the actual NMDA response and hindering a quantitative pharmacological study of NMDA antagonists. Experimental conditions were therefore worked out aimed at eliminating the $Cl^-$ current. The best protocol employed the use of Ca-free, Ba-containing solution, avoiding repetitive application of antagonists, as well as other conditions including optimal perfusion rate and optimal intervals between repetitive NMDA applications.

Several NMDA receptor blockers were tested. These compounds have very solubility and have to be dissolved in 100% dimethyl sulfoxide (DMSO) and diluted for use in ND-96 that contained 1% DMSO. Therefore, the effect of 1% DMSO on the response to $10^{-4}$M NMDA and $5 \times 10^{-6}$M glycine was examined. DMSO had no effect on NMDA response in three different cells.

Eight putative NMDA antagonists of the HU group, including 270, 271 and 259 were tested for anti-NMDA activity at a glutamate receptor. An in-depth pharmacological characterization of the antagonist activity of HU-210, 211 and 259 at the NMDA receptor was also performed. In addition, selected members of the HU group were tested for their effects on AMPA/kainate, metabotropic glutamate (quisqualate), and GABA receptors. All the HU compounds, except 210, were found to block the NMDA response to various extents. The rank order of potency of the HU group compounds in inhibiting the NMDA response was: 211=259>270>271>>210 (Table 2). Compounds HU-211 and HU-259 were shown to be non-competitive NMDA antagonists using Lineweaver-Burke analysis. The most potent NMDA antagonists, HU-211 and HU-259, had no effect on GABA or kainate responses and did not inhibit the activity of voltage-dependent P-type calcium channels expressed in oocytes injected with rat brain RNA. Inhibitory activity of HU-211 and HU-259 was first apparent at 10 nM and reached more than 40% inhibition at 1–10 μM. In parallel experiments performed on oocytes of the same frogs, HU-210 did not have any inhibitory effects on NMDA response at concentrations up to 10 μM. It is concluded that some compounds of the HU series are non-competitive NMDA inhibitors; in particular, HU-259 is one of the most potent in the series and selective for the NMDA over AMPA/kainate receptors.

TABLE 2

Effects of the HU series compounds on NMDA response in Xenopus oocytes

| Compound tested | Conc. μM | No. oocytes tested | % inhibition of NMDA |
|---|---|---|---|
| HU-211 | 1 | 12 | 32 |
| HU-211 | 10 | 4 | 47 |
| HU-210 | 10 | 6 | 0 |
| HU-259 | 1 | 4 | 35 |
| HU-259 | 10 | 8 | 41 |
| HU-270 | 1 | 12 | 20 |
| HU-271 | 1 | 6 | 16 |
| HU-271 | 10 | 10 | 20 |

PHARMACOLOGICAL EXAMPLE 13

Prevention of NMDA neurotoxicity in mice

Bicyclic compounds of the present invention were tested for their ability to block NMDA toxicity in mice. Balb/C mice received NMDA by subcutaneous injection at a dose of 60 mg/kg which was determined to be the $LD_{20}$ dose of this substance. Thirty minutes prior to injection of the neurotoxin the animals received either (a) an intravenous injection of the test drug formulated in submicronized emulsion as described in Example 11); (b) an intraperitoneal injection of the test drug dissolved in MCT oil; (c) or the appropriate vehicle alone (control groups). The mice were placed in individual cages and clinical signs were observed and scored according to the system tabulated in Table 3. The improvement rate afforded by the test drug was defined as the difference between scores of animals receiving the formulated drug and those receiving the vehicle alone. The doses tested for HU-254, HU-259 and HU-260 ranged from 5 to 30 mg/kg.

At least 6–8 mice were included per test group. The materials were tested in a masked study to preclude bias of the observer of clinical symptoms.

The bicyclic compounds HU-254, HU-259, HU-260, HU-270 and HU-271 were all found to exert neuroprotective effects with a maximum improvement of neurological scores of about 30–40% (FIG. 1). The least active compound of this series was HU-254, which exerted a maximum improvement rate of 25% on the neurological scores at an i.p. dose of 20 mg/kg. The performance of this compound was significantly enhanced by i.v. administration. For the other compounds tested clinical outcome was not significantly different for the two routes of administration tested.

TABLE 3

Neurological Scoring System NMDA Neurotoxicity in mice

| Neurological behavior | Score (s) |
|---|---|
| Straub Tail (abnormal tail posture) | 1 |
| Tail Flick | 2 |
| Tail Bite | 3 |

TABLE 3-continued

Neurological Scoring System NMDA Neurotoxicity in mice

| Neurological behavior | Score (s) |
|---|---|
| Hyperactivity | 3 |
| Tremor | 5 |
| Running | 6 |
| Circling | 6 |
| Jumping | 8 |
| Convulsions | 9 |
| Death | 15 |

Neurological—Clinical Status Calculating Method

The behavioral scoring method (tabulated above) was used as the basic quantitative procedure for evaluating the level of NMDA or kainic acid neurotoxicity in mice. The neurological clinical status of each animal was calculated by totalling the scores of all signs that were evident throughout the study. Duration of symptoms was also taken into account.

If duration of a neurological system is up to 30 seconds, the score is s−1. Duration between 0.5–3.0 mins, the score is s. Duration longer than 3 mins, the score is s+1.

PHARMACOLOGICAL EXAMPLE 14

Neuroprotection against cerebral ischemia in gerbils

The bicyclic compounds of the present invention were tested for their ability to prevent neurological damage in gerbils exposed to bilateral common carotid artery occlusion.

Mongolian gerbils (male), 65–70 gr (Tumblebrook Farm) underwent the ischemic procedure while anaesthetised with equithisine.

Common carotid arteries (CCA) were isolated and 3-0 silk suture material was positioned loosely round them. The tips of each loop were tied together, and the suture material was buried beside the trachea. The ventral neck incision was then sutured. In the following day, they were lightly anaesthetised with ether, the neck skin wounds were opened and both CCA were occluded for 10 minutes using small artery clips. During the ischemia and until the animals recovered (regaining righting reflexes), they were maintained in a warm state (36.5°–37.5° C. rectal temperature). Thirty minutes following onset of ischemia, animals were reanaesthetised (ether) and the appropriate drug was administered I.V. via the femoral vein.

Clinical evaluation. Three to 5 hours later, animals were observed for their clinical appearance using the Rudolphi method (Rudolphi et al., Cereb. Blood Flow Metab. 7:74, 1987). This was done every 24 hours, for the entire 96-hour period. At the end of this period, animals were anaesthetised (equithisine) and infused transcardially with 10% formaldehyde solution.

Histopathological evaluation. Brains were removed and stored for one week. Then, 5 μm sections were cut from the area of the dorsal hippocampus, stained with H&E and cresyl violet, and evaluated according to the following system. The number of viable pyramidal cells in the medial, middle and lateral CA1 subfield of the hippocampus were counted under 400X magnification, along 0.4 mm in both sides.

The study paradigm was (n=10): untreated animals, vehicle treated animals (SME, 4 ml/kg i.v.); and animals treated with the test drug (8 mg/kg I.V.)

Statistics. Neuroclinical appearance was analyzed using Wilcoxon Rank Sum Test. The histopathological evaluation was analyzed using One-Way ANOVA followed by Duncan's Test.

Gerbils were scored for their clinical symptoms following the ischemic insult according to the system described by Rudolphi et al. (Table 4). Each animal was evaluated daily over 4 consecutive days (Day 1 being the day of CCA occlusion). The results obtained with HU-259 are presented in FIG. 3a. The HU-259 treated group demonstrated statistically significant improvement compared to controls over the three consecutive days of observation. At three days post-ischemia 90% of the animals in the HU-259 treated group showed no signs whatsoever and 10% showed only mild signs. Histopathological damage in the HU-259 treated group was also significantly decreased compared to control groups. The gerbil global forebrain ischemia model was performed with two additional test compounds of the present invention. FIG. 3b presents data for HU-270 and HU-271 treated animals. In this case, the test compounds were dissolved in hydroxy propyl β-cyclodextrin (HPCD).

TABLE 4

Neurobehavioral scores in stroke model in gerbils (normal score, 0)

| Neurological behavior | Score (s) |
|---|---|
| Normal | 0 |
| Sleepy/lethargic | 1 |
| Hyperactive | 2 |
| Circling/Ptosis | 3 |
| Jumping | 4 |
| Tossing seizures/Ophistolonus | 5 |
| Tonic convulsion | 6 |
| Coma, weak pain response | 7 |
| Coma, no pain response | 8 |
| Death | 9 |

Modification of Rudolphi's (ref.) Clinical scoring method.

PHARMACOLOGICAL EXAMPLE 15

Neuroprotectant activity against mediated via glutamate receptors in cortical cultures.

The neuroprotective effects of the compounds of the invention were tested on neurons exposed to various excitotoxins in culture. The compounds tested included HU-259, HU-260, HU-270 and HU-271, which were all shown to have NMDA antagonist properties in mice (Example 13).

The test drugs were examined for their ability to protect neurons in culture from toxic effects of agonists of the different glutamate receptor subtypes (agonists of ionotropic and/or metabotropic glutamate receptors), e.g. NMDA, AMPA, kainate and quisqualate. The culture conditions and assay conditions were all performed as described in Eshhar et al. (NeuroReport 5, No. 3, 1993). In brief, primary cerebral cortical cell cultures were prepared from 18–20 day old rat fetuses by enzymatic dissociation. Resulting cell suspensions were plated on confluent cortical glial cell feder layer (prepared 2 weeks earlier by a similar method). Neurons were grown in MEM media containing 0.6% glucose, FUDR/Uridine mixture and $N_2$ supplement (insulin, progesterone, putrescine, selenium and transferrin). Cells at 10 days in culture were exposed to the various toxins either alone, or in the presence of the tested compounds. All exposures were carried out at 37° C. for 20–24 hours before assessing neuronal cell damage and neuroprotectant activity. Cell viability was determined morphologically following neuron specific enolase immunostaining of cells using the ABC biotin-avidin complex method, and determined quantitatively by measuring the extent of mitochondrial activity in living cells using the XTT-based assay. XTT is reduced by mitochondrial dehydrogenase to a soluble colored formazan. The density of color formation (O.D.), which is proportional to mitochondrial activity, was measured by a plate ELISA reader. The extent of neuroprotectant activity is expressed as % of cells rescued by the drugs tested.

The analogs examined in this system included HU-259, HU-270 and HU-271.

Results

| % of cells rescued from NMDA-induced toxicity (1000 µM) | |
|---|---|
| HU-270 (10 µM) | 0% |
| HU-259 (10 µM) | 100% |
| Concentration dependence of HU-271 blockade of NMDA-induced neurotoxicity (1000 µM) | |
| HU-271 (10 µM) | 100% |
| HU-271 (5 µM) | 68% |
| HU-271 (2 µM) | 27% |
| HU-271 (1 µM) | 25% |

Neuroprotectant activity of HU-259 (10 µM)—was assessed using orphological criteria only. Morphological observations (as determined by neuron specific enolase immunostaining) clearly indicated complete neuroprotection (100%).

| % of cells rescued from quisqualate-induced toxicity (500 µM) | |
|---|---|
| HU-271 (10 µM) | 37% |

PHARMACOLOGICAL EXAMPLE 16

The association of pinene derivatives with acetylcholine-muscarinic receptor and with MK-801 sites located at the NMDA receptor ion channel.

Binding studies. Interactions between test compounds and the muscarinic receptor were analyzed by the ability of 4-phenyl pinene derivatives to inhibit the binding of tritiated quinuclidinyl benzylate (QNB) to rat forebrain membranes.

Inhibition of $^3$[H]MK-801 binding to rat forebrain membranes by the test HU-211 compounds was carried out as described for HU-211 in Eshhar et al., NeuroReport 5, No. 3, 1993) (Methods section). The test compounds were solubilized in a mixture of ethanol:Emulfor:water (20:3:57).

Inhibition of [$^3$H]QNB binding to membranes by 4-phenyl pinene derivatives was determined while analogs were solubilized in alcohol only.

HU-211 analogs tested: HU-271, HU-259 and HU-254.

Results are presented in Table 5:

TABLE 5

| | % inhibition of tritiated ligand binding to membranes by 100 µM analogue | |
|---|---|---|
| Analogue | $^3$[H]QNB | $^3$[H]-MK-801 |
| HU-271 | 98.3 | 46.3 |
| HU-259 | 98.0 | 90.0 |
| HU-254 | 96.1 | 5.3 |

Concentration dependence of HU-259 (1–100 µM) inhibition of $^3$[H]MK-801 binding to rat forebrain membranes: The inhibition constant ($K_i$) value displayed by HU-259 was measured and found to be: 7.6 µM (value was obtained from a representative experiment performed in triplicate). For comparison the $K_i$ of HU-211 was determined to be 11.3 µM.

PHARMACOLOGICAL EXAMPLE 17

Increased survival of mice exposed to Hypobaric Anoxia.

Hypobaric Anoxia was used as a system for testing the neuroprotective effects of test compounds, HU-270 and HU-271. The experimental paradigm was derived from that described by Gotti and Depoortere, Congres de Circ. Cerebrale, Toulouse, 105–107 (1979). Briefly, mice in groups of 5 were placed in a chamber which was equilibrated at an atmospheric pressure of 200 mmHg (by evacuation via a vacuum pump). The mice were observed until they stopped breathing and the time was recorded for each mouse. The test compounds were administered 45 min before introducing the animals into the chamber. In all cases the experiment was performed in a masked vehicle controlled study to avoid bias on the part of the observer. Each mouse received the drug dissolved in MCT oil intraperitoneally at a dose of 5 mg/kg, or the vehicle alone (MCT oil, 5 ml/kg). The results clearly indicate a statistically significant increase of survival time in animals pretreated with the compounds of the present invention (FIG. 2b).

While the present invention has been described hereinabove with regard to various specific embodiments in order to enable those skilled in the art to practice said invention in all of its many aspects, it is to be understood that such specific embodiments are presented for the sake of illustration only, and applicants intend to be limited only by the spirit and scope of their invention as defined in the appended claims.

We claim:

1. A compound of the formula

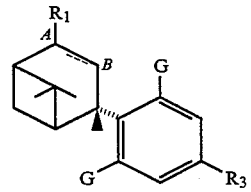

having the (3S,4S) configuration and which is essentially free of the (3R,4R) enantiomer, wherein
the dotted line A - - - B indicates an optional bond,
$R_1$ is
(a) —R'N(R")$_2$ wherein R' is $C_1$-$C_5$ alkyl and each R", which may be the same or different, is hydrogen or $C_1$-$C_5$ alkyl optionally containing a terminal —OR''' or —OC(O)R''' moiety wherein R''' is hydrogen or $C_1$-$C_5$ alkyl,
(b) —Q wherein Q is a heterocyclic moiety having a labile hydrogen atom so that said moiety acts as a carboxylic acid analogue,
(c) —R'X wherein R' is $C_1$-$C_5$ alkyl and X is halogen,
(d) —R'C(O)N(R")$_2$ wherein R' is a direct bond or $C_1$-$C_5$ alkyl and each R", which may be the same or different, is hydrogen or $C_1$-$C_5$ alkyl optionally containing a terminal —OR''' or —OC(O)R''' moiety wherein R''' is hydrogen or $C_1$-$C_5$ alkyl, or
(e) —R'C(O)OR" wherein R' is a direct bond or $C_1$-$C_5$ alkyl and R" is hydrogen or $C_1$-$C_5$ alkyl optionally containing a terminal —OR''' or —OC(O)R''' moiety wherein R''' is hydrogen or $C_1$-$C_5$ alkyl, G is (a) halogen, (b) $C_1$-$C_5$ alkyl, or (c) —$OR_2$, wherein $R_2$ is (a') —R'', wherein R'' is hydrogen or $C_1$-$C_5$ alkyl optionally containing a terminal —OR''' or —OC(O)R''' wherein R''' is hydrogen or $C_1$-$C_5$ alkyl, (b') —C(O)OR''' wherein R''' is as previously defined, or (c') —C(O)R''' wherein R''' is as previously defined, and $R_3$ is (a) $C_1$-$C_{12}$ alkyl, (b) —OR'''', in which R'''' is a straight chain or branched $C_2$-$C_9$ alkyl which may be substituted at the terminal carbon atom by a phenyl group, or (c) —$(CH_2)_n$OR''' wherein n is an integer of 1 to 7 and R''' is hydrogen or $C_1$-$C_5$ alkyl.

2. The compound of claim 1 wherein $R_3$ is 1,1-dimethylheptyl or 1,2-dimethylheptyl.

3. The compound of claim 1 wherein Q is a saturated or unsaturated ring of 4 to 8 members consisting of C with at least one of N, S, and O, said ring being optionally substituted with —COR''' or —COOR''' wherein R''' is as previously defined.

4. The compound of claim 3 wherein $R_1$ is tetrazol-5-yl.

5. The compound of claim 1 wherein A - - - B is a covalent bond, $R_1$ is —C(O)N(R'')$_2$ or —C(O)OR'', $R_2$ is —C(O)R''', and $R_3$ is $C_5$-$C_{12}$ alkyl.

6. The compound of claim 1 wherein $R_1$ is COOH.

7. The compound of claim 1 wherein $R_2$ is acetyl.

8. The compound of claim 1 having the formula

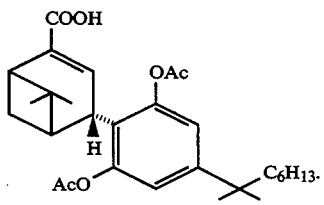

9. The compound of claim 6, wherein $R_2$ is hydrogen and $R_3$ is 1,1-dimethylheptyl or 1,2-dimethylheptyl.

10. The compound of claim 1 wherein $R_1$ is a carboxamide.

11. The compound of claim 10 wherein $R_1$ is an amino acid carboxamide.

12. The compound of claim 11 wherein $R_1$ is an amino acid carboxamide, $R_2$ is acetyl, and $R_3$ is 1,1-dimethylheptyl or 1,2-dimethylheptyl.

13. The compound of claim 12 wherein $R_1$ is glycine carboxamide, $R_2$ is acetyl, and $R_3$ is 1,1-dimethylheptyl or 1,2-dimethylheptyl.

14. The compound of claim 1 wherein $R_1$ is ethanol carboxamide.

15. The compound of claim 14 wherein $R_1$ is ethanol carboxamide, $R_2$ is acetyl, and $R_3$ is 1,1-dimethylheptyl or 1,2-dimethylheptyl.

16. The compound of claim 15 having the formula

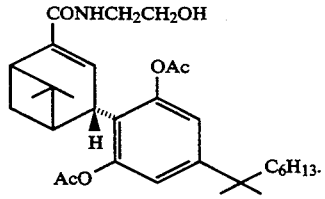

17. The compound of claim 1 wherein $R_1$ is diethylcarboxamide.

18. The compound of claim 17 wherein $R_1$ is diethylcarboxamide, $R_2$ is acetyl, and $R_3$ is 1,1-dimethylheptyl or 1,2-dimethylheptyl.

19. The compound of claim 18 having the formula

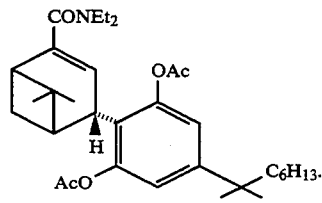

20. A pharmaceutical composition having analgesic, anti-emetic, sedative, anti-inflammatory, anti-glaucoma, or neuroprotective activities which contains as an active ingredient a therapeutically effective quantity of a compound of claim 1.

21. A pharmaceutical composition with neuroprotectant activity containing as active ingredient an effective quantity of a compound of general formula:

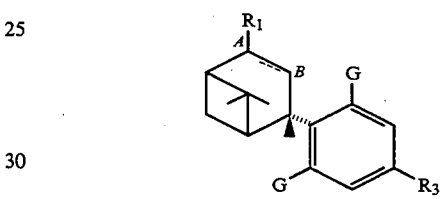

having the (3S,4S) configuration and which is essentially free of the (3R,4R) enantiomer, wherein
the dotted line A - - - B indicates an optional bond,
$R_1$ is
(a) —R'N(R'')$_2$ wherein R' is $C_1$-$C_5$ alkyl and each R'', which may be the same or different, is hydrogen or $C_1$-$C_5$ alkyl optionally containing a terminal —OR''' or —OC(O)R''' moiety wherein R''' is hydrogen or $C_1$-$C_5$ alkyl,
(b) —Q wherein Q is a heterocyclic moiety having a labile hydrogen atom so that said moiety acts as a carboxylic acid analogue,
(c) —R'X wherein R' is $C_1$-$C_5$ alkyl and X is halogen,
(d) —R'C(O)N(R'')$_2$ wherein R' is a direct bond or $C_1$-$C_5$ alkyl and each R'', which may be the same or different, is hydrogen or $C_1$-$C_5$ alkyl optionally containing a terminal —OR''' or —OC(O)R''' moiety wherein R''' is hydrogen or $C_1$-$C_5$ alkyl,
(e) —R'C(O)OR'' wherein R' is a direct bond or $C_1$-$C_5$ alkyl and R'' is hydrogen or $C_1$-$C_5$ alkyl optionally containing a terminal —OR''' or —OC(O)R''' moiety wherein R''' is hydrogen or $C_1$-$C_5$ alkyl,
(f) —R' wherein R' is $C_1$-$C_5$ alkyl, or
(g) —R'OR''' wherein R' is $C_1$-$C_5$ alkyl and R''' is hydrogen or $C_1$-$C_5$ alkyl,
G is halogen, $C_1$-$C_5$ alkyl, or —$OR_2$ wherein $R_2$ is R'', wherein R'' is hydrogen or $C_1$-$C_5$ alkyl optionally containing a terminal —OR''' or —OC(O)R''' moiety wherein R''' is hydrogen or $C_1$-$C_5$ alkyl, —C(O)OR''' wherein R''' is as previously defined, or —C(O)R''' wherein R''' is as previously defined, and R₃ is (a) $C_1$-$C_{12}$ alkyl, (b) —OR'''', in which R'''' is a straight chain or branched $C_2$-$C_9$ alkyl which may be substituted at the terminal carbon atom by a phenyl group, or (c) —(CH₂)ₙOR''' wherein n is an integer of 1 to 7 and R''' is hydrogen or $C_1$-$C_5$ alkyl.

22. A pharmaceutical composition according to claim 20 wherein the active ingredient is (+)-4-[4-(1,1-dimethylheptyl)-2,6-diacetoxyphenyl]-2-carboxy-6,6-dimethyl-bicyclo[3.1.1] hept-2-en. (1H-α; 5H-α; 4H-β).

23. A pharmaceutical composition according to claim 20 wherein the active ingredient is (+)-4-[4-(1,1-dimethylheptyl)-2,6-diacetoxyphenyl]-2-N,N-diethyl-carboxamide)-6,6-dimethyl-bicyclo[3.1.1]hept-2-en.(1H-α; 5H-α; 4H-β).

24. A pharmaceutical composition according to claim 20 wherein the active ingredient is (+)-4-[4-(1,1-dimethylheptyl)-2,6-diacetoxyphenyl]-2-N-ethanolcarboxamide)-6,6-dimethyl-bicyclo[3.1.1]hept-2-en. (1H-α; 5H-α; 4H-β).

25. A pharmaceutical composition according to one of claims 22–24 containing a pharmaceutically acceptable diluent or carrier.

26. A pharmaceutical composition according to claim 25 wherein the diluent is an aqueous cosolvent solution comprising a pharmaceutically acceptable cosolvent, a micellar solution prepared with natural or synthetic ionic or nonionic surfactants, or a combination of such cosolvent and micellar solutions.

27. A pharmaceutical composition according to claim 25 which comprises a carrier consisting essentially of a solution of ethanol, a surfactant, and water.

28. A pharmaceutical composition according to claim 25 which comprises a carrier consisting essentially of an emulsion comprising triglycerides, lecithin, glycerol, an emulsifier, an antioxidant, and water.

29. A pharmaceutical composition according to one of claims 22–24 in unit dosage form.

30. A pharmaceutical composition according to claim 29 wherein the daily dosage of said compound is between about 0.1 and 50 mg/kg.

31. A pharmaceutical composition according to claim 30 wherein the daily dosage of said compound is between about 1 and 20 mg/kg.

32. A method of treatment of injuries to the central nervous system associated with excitatory amino acid neurotoxicity, which comprises administering to a patient a therapeutically effective amount of a pharmaceutical composition containing as active ingredient an effective quantity of a compound of general formula:

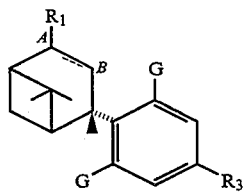

having the (3S,4S) configuration and which is essentially free of the (3R,4R) enantiomer, wherein
the dotted line A - - - B indicates an optional bond,
R₁ is
(a) —R'N(R'')₂ wherein R' is $C_1$-$C_5$ alkyl and each R'', which may be the same or different, is hydrogen or $C_1$-$C_5$ alkyl optionally containing a terminal —OR''' or —OC(O)R''' moiety wherein R''' is hydrogen or $C_1$-$C_5$ alkyl,
(b) —Q wherein Q is a heterocyclic moiety having a labile hydrogen atom so that said moiety acts as a carboxylic acid analogue,
(c) —R'X wherein R' is $C_1$-$C_5$ alkyl and X is halogen,
(d) —R'C(O)N(R'')₂ wherein R' is a direct bond or $C_1$-$C_5$ alkyl and each R'', which may be the same or different, is hydrogen or $C_1$-$C_5$ alkyl optionally containing a terminal —OR''' or —OC(O)R''' moiety wherein R''' is hydrogen or $C_1$-$C_5$ alkyl,
(e) —R'C(O)OR'' wherein R' is a direct bond or $C_1$-$C_5$ alkyl and R'' is hydrogen or $C_1$-$C_5$ alkyl optionally containing a terminal —OR''' or —OC(O)R''' moiety wherein R''' is hydrogen or $C_1$-$C_5$ alkyl,
(f) —R' wherein R' is $C_1$-$C_5$ alkyl, or
(g) —R'OR''' wherein R' is $C_1$-$C_5$ alkyl and R''' is hydrogen or $C_1$-$C_5$ alkyl,
G is halogen, $C_1$-$C_5$ alkyl, or —OR₂ wherein R₂ is R'', wherein R'' is hydrogen or $C_1$-$C_5$ alkyl optionally containing a terminal —OR''' or —OC(O)R''' moiety wherein R''' is hydrogen or $C_1$-$C_5$ alkyl, —C(O)OR''' wherein R''' is as previously defined, or —C(O)R''' wherein R''' is as previously defined, and
R₃ is (a) $C_1$-$C_{12}$ alkyl, (b) —OR'''', in which R'''' is straight chain or branched $C_2$-$C_9$ alkyl which may be substituted at the terminal carbon atom by a phenyl group, or (c) —(CH₂)ₙOR''' wherein n is an integer of 1 to 7 and R''' is hydrogen or $C_1$-$C_5$ alkyl.

33. A method for blocking N-methyl-D-aspartate (NMDA) receptors in a patient which comprises administering to said patient a therapeutically effective amount of a pharmaceutical composition containing as active ingredient an effective quantity of a compound of general formula:

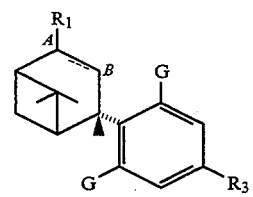

having the (3S,4S) configuration and which is essentially free of the (3R,4R) enantiomer, wherein
the dotted line A - - - B indicates an optional bond,
R₁ is
(a) —R'N(R'')₂ wherein R' is $C_1$-$C_5$ alkyl and each R'', which may be the same or different, is hydrogen or $C_1$-$C_5$ alkyl optionally containing a terminal —OR''' or —OC(O)R''' moiety wherein R''' is hydrogen or $C_1$-$C_5$ alkyl,
(b) —Q wherein Q is a heterocyclic moiety having a labile hydrogen atom so that said moiety acts as a carboxylic acid analogue,
(c) —R'X wherein R' is $C_1$-$C_5$ alkyl and X is halogen,
(d) —R'C(O)N(R'')₂ wherein R' is a direct bond or $C_1$-$C_5$ alkyl and each R'', which may be the same or different, is hydrogen or $C_1$-$C_5$ alkyl optionally containing a terminal —OR''' or —OC- (O)R''' moiety wherein R''' is hydrogen or $C_1$-$C_5$ alkyl,
(e) —R'C(O)OR'' wherein R' is a direct bond or $C_1$-$C_5$ alkyl and R'' is hydrogen or $C_1$-$C_5$ alkyl optionally containing a terminal —OR''' or —OC(O)R''' moiety wherein R''' is hydrogen or $C_1$-$C_5$ alkyl,
(f) —R' wherein R' is $C_1$-$C_5$ alkyl, or
(g) —R'OR''' wherein R' is $C_1$-$C_5$ alkyl and R''' is hydrogen or $C_1$-$C_5$ alkyl,
G is halogen, $C_1$-$C_5$ alkyl, or —OR$_2$ wherein $R_2$ is R'', wherein R'' is hydrogen or $C_1$-$C_5$ alkyl optionally containing a terminal —OR''' or —OC(O)R''' moiety wherein R''' is hydrogen or $C_1$-$C_5$ alkyl, —C(O)OR''' wherein R''' is as previously defined, or —C(O)R''' wherein R''' is as previously defined, and
$R_3$ is (a) $C_1$-$C_{12}$ alkyl, (b) —OR'''', in which R'''' is a straight chain or branched $C_2$-$C_9$ alkyl which may be substituted at the terminal carbon atom by a phenyl group, or (c) —$(CH_2)_n$OR''' wherein n is an integer of 1 to 7 and R''' is hydrogen or $C_1$-$C_5$ alkyl.

* * * * *